(12) United States Patent
Warfield et al.

(10) Patent No.: US 10,782,376 B2
(45) Date of Patent: Sep. 22, 2020

(54) DIFFUSION-WEIGHTED MRI USING MULTIPLE B-VALUES AND CONSTANT ECHO TIME

(71) Applicant: Children's Medical Center Corporation, Boston, MA (US)

(72) Inventors: Simon K. Warfield, Brookline, MA (US); Benoit Scherrer, Cambridge, MA (US)

(73) Assignee: Children's Medical Center Corporation, Boston, MA (US)

( * ) Notice: Subject to any disclaimer, the term of this patent is extended or adjusted under 35 U.S.C. 154(b) by 1237 days.

(21) Appl. No.: 14/431,536

(22) PCT Filed: Sep. 27, 2013

(86) PCT No.: PCT/US2013/062230
§ 371 (c)(1),
(2) Date: Mar. 26, 2015

(87) PCT Pub. No.: WO2014/052782
PCT Pub. Date: Apr. 3, 2014

(65) Prior Publication Data
US 2015/0253410 A1  Sep. 10, 2015

Related U.S. Application Data

(60) Provisional application No. 61/707,745, filed on Sep. 28, 2012.

(51) Int. Cl.
*G01R 33/563* (2006.01)
*A61B 5/055* (2006.01)
(Continued)

(52) U.S. Cl.
CPC ........ *G01R 33/56341* (2013.01); *A61B 5/055* (2013.01); *G01R 33/385* (2013.01); *G01R 33/5602* (2013.01); *G01R 33/5608* (2013.01)

(58) Field of Classification Search
CPC .............. G01R 33/385; G01R 33/5602; G01R 33/5608; G01R 33/56341; A61B 5/055
(Continued)

(56) References Cited

U.S. PATENT DOCUMENTS 5,281,914 A * 1/1994 Conturo ............... G01R 33/563
                                                              324/309
10,509,089 B2 * 12/2019 Feiweier ............ G01R 33/5608
(Continued)

OTHER PUBLICATIONS

Yeh et al., "Reduced Encoding Diffusion Spectrum Imaging Implemented With a Bi-Gaussian Model" IEEE Transactions on Medical Imaging, vol. 27, No. 10, Oct. 2008, pp. 1415-1424.
(Continued)

*Primary Examiner* — Steven L Yeninas
(74) *Attorney, Agent, or Firm* — Wolf, Greenfield & Sacks, P.C.

(57) ABSTRACT

Methods and apparatus for acquiring diffusion-weighted images. The method comprises selecting a plurality of diffusion gradient vectors, wherein at least two of the plurality of diffusion gradient vectors correspond to different non-zero b-values. The method further comprises determining a gradient strength for each of the plurality of diffusion gradient vectors such that an echo image time (TE) remains constant when gradients corresponding to each of the plurality of diffusion gradient vectors are applied. The method further comprises acquiring the diffusion-weighted images using a gradient encoding scheme including the gradients corresponding to each of the plurality of gradient vectors.

20 Claims, 18 Drawing Sheets

(51) Int. Cl.
*G01R 33/385* (2006.01)
*G01R 33/56* (2006.01)

(58) Field of Classification Search
USPC ........................................................ 324/309
See application file for complete search history.

(56) References Cited

U.S. PATENT DOCUMENTS

| | | | |
|---|---|---|---|
| 2005/0007100 A1 | 1/2005 | Basser et al. | |
| 2005/0068031 A1* | 3/2005 | Frank ............... | G01R 33/56341 324/309 |
| 2008/0272781 A1* | 11/2008 | Chiang ............ | G01R 33/56341 324/312 |
| 2009/0096448 A1* | 4/2009 | Meredith ......... | G01R 33/56341 324/309 |
| 2011/0085722 A1* | 4/2011 | Feiweier .......... | G01R 33/56341 382/131 |
| 2012/0027283 A1 | 2/2012 | Lang et al. | |
| 2012/0062229 A1* | 3/2012 | Topgaard ......... | G01R 33/56341 324/309 |
| 2012/0194189 A1 | 8/2012 | Sun | |
| 2012/0280686 A1 | 11/2012 | White et al. | |
| 2016/0231410 A1 | 8/2016 | Warfield et al. | |

OTHER PUBLICATIONS

Kuo et al., "Optimization of diffusion spectrum imaging and q-ball imaging on clinical MRI system" NeuroImage 41 (2008) 7-18.
Nezamzadeh et al., "In-vivo investigation of the human cingulum bundle using the optimization of MR diffusion spectrum imaging" European Journal of Radiology 75 (2010) e29-e36.
Peled et al., "High b-Value Apparent Diffusion-Weighted Images From CURVE-Ball DTI" Journal of Magnetic Resonance Imaging, 30:243-248 (2009).
Scherrer et al., "Characterizing Complex White Matter Structure from Cube and Sphere Diffusion Imaging with a Multi-Fiber Model (CUSP-MFM)" Proc. Intl. Soc. Mag. Reson. Med. 19 (2011).
Scherrer et al., "Parametric Representation of Multiple White Matter Fascicles from Cube and Sphere Diffusion MRI" PLOS ONE, Nov. 2012, vol. 7, Issue 11.
Cook et al., "Optimal Acquisition Orders of Diffusion-Weighted MRI Measurements" Journal of Magnetic Resonance Imaging, 25:1051-1058 (2007).
International Search Report and Written Opinion for International Patent Application No. PCT/US2013/062230 dated Mar. 11, 2014.
International Preliminary Report on Patentability for International Application No. PCT/US2013/062230 dated Apr. 9, 2015.
International Search Report and Written Opinion for International Application No. PCT/US2014/056582 dated Dec. 16, 2014.
International Preliminary Report on Patentability for International Application No. PCT/US2014/056582 dated Mar. 31, 2016.

\* cited by examiner

DIFFUSION-WEIGHTED MRI USING MULTIPLE B-VALUES AND CONSTANT ECHO TIME

RELATED APPLICATIONS

This Application is a national stage application under 35 U.S.C. § 371 of PCT International Application No. PCT/US2013/062230, filed Sep. 27, 2013, which claims priority under 35 U.S.C. § 119(e) to U.S. Provisional Patent Application Ser. No. 61/707,745 filed Sep. 28, 2012, each of which is herein incorporated by reference in its entirety.

GOVERNMENT SUPPORT

This invention was made with government support under grant numbers R01 RR021885, R01 EB008015, R03 EB008680, R01 LM010033, R42 MH086984 and UL1 RR025758 awarded by the National Institutes of Health. The government has certain rights in the invention.

BACKGROUND

Magnetic resonance imaging (MRI) includes techniques for capturing data related to the internal structure of an object of interest, for example, by non-invasively obtaining images of internal structure of the human body, and has been widely used as a diagnostic tool in the medical community. MRI exploits the nuclear magnetic resonance (NMR) phenomenon to distinguish different structures, phenomena or characteristics of an object of interest. For example, in biological subjects, MRI may be employed to distinguish between various tissues, organs, anatomical anomalies (e.g., tumors), and/or to image diffusion, blood flow, blood perfusion, etc.

In general, MRI operates by manipulating spin characteristics of subject material. MRI techniques include aligning the spin characteristics of nuclei of the material being imaged using a generally homogeneous magnetic field and perturbing the magnetic field with a sequence of radio frequency (RF) pulses. To invoke the NMR phenomenon, one or more resonant coils may be provided proximate an object positioned within the magnetic field. The RF coils are adapted to generate RF pulses, generally in the form of RF pulse sequences adapted for a particular MRI application, to excite the nuclei and cause the spin to precess about a different axis (e.g., about an axis in the direction of the applied RF pulses). When an RF pulse subsides, spins gradually realign with the magnetic field, releasing energy that can be measured to capture NMR data about the internal structure of the object.

Measuring water diffusion with magnetic resonance diffusion-weighted imaging (MR-DWI) has enabled non-invasive investigation and characterization of the white matter architecture and microstructure in the brain. Diffusion in a white matter fascicles has been observed to be highly anisotropic, with primary orientation of the diffusion corresponding to the orientation of the fascicle. The underlying microstructure that gives rise to this anisotropy has been investigated. Diffusion tensor imaging (DTI) was proposed to describe the three-dimensional nature of anisotropic diffusion. Assuming homogeneous Gaussian diffusion, within each voxel, DTI describes the magnitude and orientation of water molecule diffusion with a second-order tensor estimated from diffusion measurements in several directions. More precisely, DTI relates the measured diffusion-weighted signal $S_k$, along a gradient direction $g_k$ to the non-attenuated signal $S_0$ via the Stejskal-Tanner equation:

$$S_k(D) = S_0 e^{-TE/T2} e^{-\gamma^2 \delta^2 (\Delta - \delta/3) g_k^T D g_k} \quad (1)$$

where TE is the echo time, T2 the T2 relaxation time of the tissue, $\gamma$ the gyromagnetic ratio, $\delta$ and $\Delta$ the diffusion sensitizing pulse gradients duration and time separation, and D is the 3×3 diffusion tensor.

The applied b-value defined by $b_k = \gamma^2 \delta^2 (\Delta - \delta/3) G_k^2$, which depends on the gradient strength $G_k^2 = \|g_k\|^2$, has been introduced to simplify the notations in equation (1) and describes the diffusion sensitization strength. The nominal b-value $b_{nominal} = \gamma^2 \delta^2 (\Delta - \delta/3)$ describes the b-value for the unit-norm gradients. The term $e^{-TE/T2}$ is generally considered constant across all gradients and omitted. However, and importantly, this term highlights how the signal amplitude $S_k(D)$ decreases exponentially for increasing TE.

DTI and its underlying mono-exponential signal attenuation assumption are generally considered to satisfactorily represent single fascicles when imaging with b-values lower than 3000 s/mm², which is frequently the case in clinical settings. Non-monoexponential behavior of the signal at a voxel in this b-value range can arise from cerebral spinal fluid (CSF) partial voluming, mixtures of fascicles present in the voxel and other sources. The diffusion tensor enables representation of the orientation of a single fascicle as well as the characterization of the diffusion process. Tensor parameters such as the fractional anisotropy (FA), the mean diffusivity (MD), the axial diffusivity (AD), and the radial diffusivity (RD) can be computed, and have been shown to provide valuable information that reflects changes in the white matter due to development, disease and degeneration. DTI requires relatively short acquisition times and has been successfully employed in clinical studies.

DTI has been shown to be a poor parametric model for representing the diffusion signal arising at voxels that encompass multiple fascicles with heterogeneous orientation such as fascicle crossing, kissing or fanning. Several approaches have been investigated to overcome this fundamental limitation, which involve various diffusion signal sampling schemes and ways to analyze the diffusion signal as detailed below.

Cartesian sampling and spherical sampling are two q-space sampling strategies that have been used for complex fiber structure assessment. Cartesian sampling is used by diffusion spectrum imaging (DSI). Spherical sampling as employed in high angular resolution imaging (HARDI) techniques reduces the imaging time and requires imaging gradients with moderate intensity. Several HARDI-based techniques have been proposed, as discussed in further detail below. Single-shell HARDI acquisitions with a single non-zero b-value have been considered to image a sphere of constant radius in q-space. Multiple-shell HARDI acquisitions that enable the acquisition of multiple non-zero b-values by combining in a single acquisition, the sampling of multiple shells of different radius in q-space, have also been proposed.

Other sampling techniques have been proposed for reasons other than assessing complex fiber structures. For example, sampling using the tetrahedral √3-norm gradients has been employed to measure the apparent diffusion coefficient (ADC) from four diffusion measurements. Because $b_k = b_{nominal} G_k^2$ this technique enables imaging at higher b-values than the nominal b-value without modifying the timing parameters $\delta$ and $\Delta$, but by using gradients with norm greater than one. It provides the optimal minimum achievable TE for the corresponding applied b-value, leading to a better SNR and potentially to lower eddy current distortion because the diffusion gradient pulses can be shortened. Using the same concept, the six hexahedral √2-norm gradients may be used to estimate a diffusion tensor from seven measurements. Furthermore, in (CUbe Rays to Vertices and Edges) CURVE-ball, a spherical sampling and the hexahedral and tetrahedral gradients are combined to perform the estimation of a single-tensor model at three different diffusion scales $b_{nominal}$, $2b_{nominal}$, and $3b_{nominal}$.

Several approaches have been investigated to analyze the diffusion signal and represent multiple white-matter fascicles with complex geometry. Both parametric (model-based) and non-parametric (model-free) approaches have been proposed. Generally, these models focus on estimating either (1) the diffusion displacement probability density function (diffusion PDF), (2) the diffusion orientation distribution function (dODF) which is the angular profile of the diffusion PDF or (3) the fiber orientation distribution function (fODF), also known as the fiber orientation density (FOD) and which is of central interest for tractography.

Model-free approaches include diffusion spectrum imaging (DSI). In this technique, the diffusion PDF is directly estimated from the inverse Fourier transform of the measured signal, requiring a very high number of measurements to satisfy the Nyquist condition. Q-ball imaging (QBI) estimates an approximate non-parametric angular profile of the diffusion PDF without actually computing the diffusion PDF, by using the Funk-Radon transform. Fast and robust analytical QBI estimation procedures have been proposed. QBI results in the estimation of an approximated dODF related to the true dODF by modulation with a zero-order Bessel function. This leads to a spectral broadening of the diffusion peaks of individual fascicles at moderate b-values accessible on a clinical scanner, perturbing the FOD reconstruction necessary for carrying out tractography. Mixing of individual tracts in a voxel leads to local maxima that does not coincide with the true fascicle orientation, leading to a relatively low fidelity representation. To avoid the usual Q-Ball approximation, an Exact Q-Ball Imaging (EQBI), which derives a direct relationship between the dODF and the diffusion data has been proposed. EQBI enables the estimation of the exact dODF under the assumption of a Gaussian profile.

Q-space approaches such as DSI, QBI, or EQBI are limited by at least three error sources. These techniques are based on the narrow pulse approximation assumption, considering that molecules do not diffuse during the application of the diffusion sensitizing gradients. The gradient pulses are then modeled by a Dirac shape which is not practically feasible, especially on clinical systems. In practice, in clinical settings, the diffusion-encoding gradient duration $\delta$ is typically of the same order of magnitude as the time offset $\Delta$ between encoding gradients ($\Delta/\delta \approx 1$) to minimize T2 decay and to obtain better SNR, which is a very poor approximation of a Dirac shape. Additionally, since the imaging time has to be finite, only a finite region in q-space is imaged using these techniques. This has been shown to lead to a blurred propagator with decreased contrast and angular resolution. Also, these techniques are limited by the need to truncate the Fourier representation which is required to numerically compute the infinite series involved in the Fourier transformation, leading to quantization artifacts.

In contrast, parametric models describe a predetermined model of diffusion rather than an arbitrary one. They potentially require a smaller number of images to be acquired, leading to a reduced acquisition time. Several model-based approaches have been investigated. Among them, generalized diffusion tensor imaging (GDTI) models the white-matter fascicles with higher-order tensors; spherical deconvolution (SD) directly estimates the FOD instead of the dODF and has a better angular resolution; and diffusion orientation transform (DOT) employs a model-based q-space modeling based on the assumption of a monoexponential decay of the signal attenuation.

SUMMARY

Some embodiments are directed to a method of acquiring diffusion-weighted images. The method comprises selecting a plurality of diffusion gradient vectors, wherein at least two of the plurality of diffusion gradient vectors correspond to different non-zero b-values, determining a gradient strength for each of the plurality of diffusion gradient vectors such that an echo image time (TE) remains constant when gradients corresponding to each of the plurality of diffusion gradient vectors are applied, and acquiring the diffusion-weighted images using a gradient encoding scheme including the gradients corresponding to each of the plurality of gradient vectors.

Other embodiments are directed to a magnetic resonance imaging (MRI) apparatus. The MRI apparatus comprises a main magnetic field coil, a plurality of gradient magnetic field coils, and at least one computer processor programmed with a plurality of instructions that, when executed by the at least one computer processor, perform a method of operating the MRI apparatus to acquire diffusion-weighted images. The method comprises selecting a plurality of diffusion gradient vectors, wherein at least two of the plurality of diffusion gradient vectors correspond to different non-zero b-values, determining a gradient strength for each of the plurality of diffusion gradient vectors such that TE remains constant when gradients corresponding to each of the plurality of diffusion gradient vectors are applied, and acquiring, using the main magnetic field coil and the plurality of gradient magnetic field coils, the diffusion-weighted images using a gradient encoding scheme including the gradients corresponding to each of the plurality of gradient vectors.

Other embodiments are directed to a computer-readable medium, encoded with a plurality of instructions that, when executed by a computer, performs a method of selecting a plurality of diffusion gradient vectors, wherein at least two of the plurality of diffusion gradient vectors correspond to different non-zero b-values, the method comprising determining a gradient strength for each of the plurality of diffusion gradient vectors such that TE remains constant when gradients corresponding to each of the plurality of diffusion gradient vectors are applied and acquiring diffusion-weighted images using a gradient encoding scheme including the gradients corresponding to each of the plurality of gradient vectors.

It should be appreciated that all combinations of the foregoing concepts and additional concepts discussed in greater detail below (provided that such concepts are not mutually inconsistent) are contemplated as being part of the inventive subject matter disclosed herein.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 4B: CUSP-xT; FIG. 4C: CUSP-P) for determining gradients in a gradient encoding scheme in accordance with some embodiments;

DETAILED DESCRIPTION

Following below are more detailed descriptions of various concepts related to, and inventive embodiments of, methods and apparatus according to the present disclosure for acquiring diffusion-weighted images having multiple b-values. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

Figure 1:
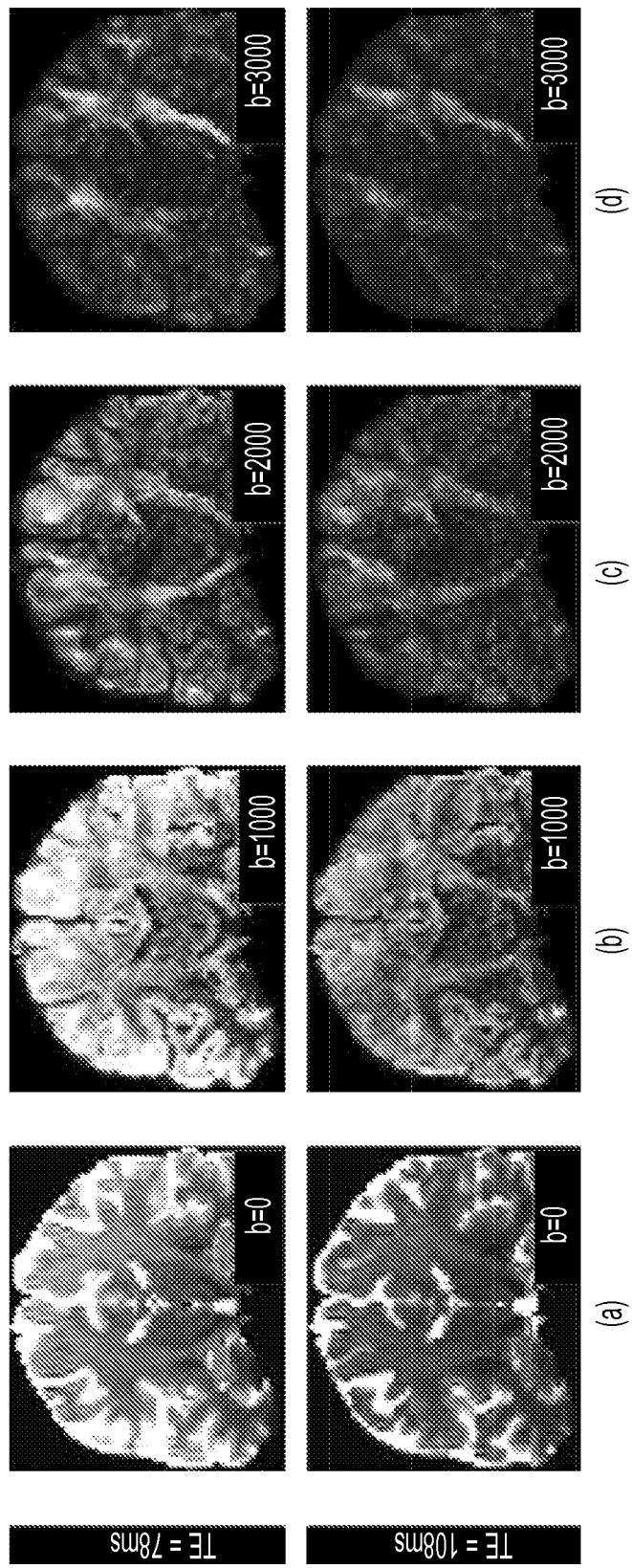
FIG. 1 illustrates diffusion-weighted images acquired using different b-values and TE.

As shown in FIG. 1, acquiring magnetic resonance images using a longer TE reduces the signal-to-noise ratio for all the measurements, regardless of the applied b-value. FIG. 1 illustrates the signal decrease when TE and the b-value increase in DWI. FIG. 1A illustrates a diffusion-weighted acquisition with b=0 s/mm². FIG. 1B illustrates a diffusion-weighted acquisition with b=1000 s/mm². FIG. 1C illustrates a diffusion-weighted acquisition with b=2000 s/mm². FIG. 1D illustrates a diffusion-weighted acquisition with b=3000 s/mm². The top line of images in FIG. 1 illustrates a diffusion-weighted acquisition with TE=78 ms obtained using a CUSP sequence, described in more detail below, with b<3000 s/mm². The bottom line of images in FIG. 1 illustrates a diffusion-weighted acquisition with TE=108 s/mm² obtained using a multi-shell HARDI sequence with b<3000 s/mm². FIG. 1 shows how the signal amplitude decreases (and so does the signal-to-noise ratio) when the b-value and the TE increase (first line versus second line). Acquisitions with a short TE should be favored, particularly when imaging at a high b-value.

The minimum achievable TE and nominal b-value follow a complex relationship via the timing parameters δ and Δ, which can be approximated by $$TE \approx \left(\frac{12 b_{nominal}}{\gamma^2}\right)^{1/3}.$$

Consequently, increasing the nominal b-value increases the minimum achievable TE, which in turn leads to an exponentially-decreased signal amplitude closer to the noise floor. Considering that the noise amplitude is constant, this signal dropout leads to a lower SNR for each diffusion-weighted (DW) image, regardless of their b-value. This leads to a fundamental trade-off in diffusion imaging: while higher b-values are known to increase the contrast between the DW gradient directions, and therefore to increase the reliability of estimation of orientation of each fascicle, higher nominal b-values also lead to a longer TE and to a lower SNR for each DW image, decreasing the estimation certainty and quality. Ideally, a diffusion-weighted acquisition should achieve a trade-off between acquiring adequate b-values while minimizing the TE to maximize the SNR.

The inventors have recognized and appreciated that the two techniques described above used for complex fiber structure assessment, Cartesian sampling and spherical sampling, have limitations that restrict their use in routine clinical practice. For example, Cartesian sampling often requires a large number N of measurements, typically 200<N<512, preventing the technique from being used in routine clinical practice. Spherical sampling, and in particular, multi-shell HARDI techniques result in a imaging echo time (TE) that depends upon the highest b-value determined based on the radius of the outer shell. The longer TE values associated with multi-shell HARDI techniques result in images with a decreased signal-to-noise ratio (SNR) for all the measurements (e.g., see equation (1) above) and result in an overall longer imaging time. In addition, imaging a higher b-value is generally achieved by using a longer diffusion gradient pulse duration, which in turn leads to larger eddy current distortion.

The inventors have recognized and appreciated that multi-tensor models cannot be fully estimated with a single-shell HARDI acquisition because the tensor size and the fraction of occupancy are collinear, leading to a system of equations with an infinite number of solutions. With images acquired using a single non-zero b-value, only the tensor orientation can be correctly estimated, but not the tensor size nor the fractions of occupancy. As discussed in more detail below, multiple non-zero b-values may be required to ensure a unique solution to and full estimation of the multi-tensor model, enabling simultaneous estimation of the tensor orientation, the tensor size, and the fractions of occupancy.

Some embodiments of the present disclosure are directed to techniques for acquiring MRI data associated with multiple non-zero b-values with little or no increase in the amount of imaging time required for a single-shell HARDI acquisition, thereby yielding an acquisition scheme that may be adopted in routine clinical practice with conventional MRI scanners. Embodiments using the acquisition scheme enable estimation of a full multi-tensor model with a relatively low maximum TE and consequently a relatively high SNR compared to multi-shell HARDI acquisition schemes. The novel acquisition technique (also called Cube and SPhere (CUSP) acquisition herein) combines aspects of a single-shell HARDI with images in an enclosing cube of constant TE. As discussed in more detail below, the enclosing cube of the shell is a cube of constant TE, in which gradients with higher b-values can be imaged without increasing the TE, by using gradients with norm greater than one. Such an acquisition technique satisfies the requirement for multiple non-zero b-values, enabling the estimation of the complete multi-tensor model. High b-values may also be incorporated to allow for better characterization of multi-compartment models. In accordance with the techniques described herein, images associated with b-values higher than the nominal b-value may be acquired while achieving the same low TE as a single-shell HARDI. Compared to a multiple-shell HARDI, CUSP acquisition described herein results in a significantly higher SNR, shorter imaging time and potentially lower eddy current distortion than previously reported acquisition techniques.

Also discussed in more detail below is a novel multi-tensor optimization technique based on the maximum a posteriori (MAP) principle. This technique combines the model estimation and the model regularization to reduce the effect of noise. The prior for the model is based on a finite difference scheme in which only tensors which are part of the same fascicle are regularized together. The model is formulated in the log-Euclidean framework, which prevents leaving the set of symmetric positive definite matrices during the optimization and ensures nondegenerate solutions. The formulation discussed in more detail below enables efficient optimization of the parameters and enables the introduction of suitable constraints on the estimated tensors.

A drawback of the diffusion-based modeling techniques described above (e.g., DSI, QBI, DOT, SD, and GDTI) is that they focus on describing the general shape of the diffusion profile in each voxel. They do not represent each fascicle independently and therefore do not characterize the proportion of each fascicle passing through a voxel. Importantly, they do not enable characterization of each fascicle. Diffusion parameters such as the generalized fractional anisotropy (GFA) can be computed but represent a DW signal dispersion property rather than an individual fascicle property. For example, a synthetic fascicle consisting of an identical tensor at every voxel crossed by another synthetic fascicle has a GFA that varies in the crossing region, which is not clinically relevant. Using the techniques described above, it is generally not possible to distinguish whether a change in diffusion parameters along a fascicle is associated with a change in the intrinsic fascicle property or because of the presence of crossing fascicles. These approaches provide information about the distribution of fascicle orientations in the voxel but are limited to connectivity assessment.

In contrast, multi-fascicle models (MFM) consider at each voxel a mixture of independent fascicles with heterogeneous orientation. Making the assumption of a slow exchange between the fascicles' compartments, the diffusion signal in each voxel is modeled as a mixture of the diffusion signal arising from each individual fascicle. Integration of an isotropic component has also been investigated to model the diffusion of unrestricted water. This enables characterization of pathologies such as edema, stroke, or inflammation. This also enables characterization of the CSF contamination due to partial volume effect, known to perturb the accurate estimation of the anisotropic diffusion compartments. Ultimately, the diffusion-weighted signal $S_k$ along a gradient direction $g_k$ for MFM with an isotropic compartment and $N_f$ fascicles can be described by the following general mixture;

$$S_k(D, f) = S_0 \left( f_0 S_k^{free\_water} + \sum_{j=1}^{N_f} f_j S_{k,j}^{single\_fascile} \right), \quad (2)$$

where $S_{k,j}^{single\_fascile}$ is the diffusion signal arising from a single fascicle, $S_k^{free\_water}$ is the diffusion signal arising from the unrestricted water diffusion, and $f=(f_0, \ldots, f_{N_f})$ describes the fractions of occupancy of each compartment ($f_j \in [0,1]$) and sum to one.

The diffusivity of free water is generally considered to be well modeled by an isotropic Gaussian distribution, leading to $S_k^{free\_water} = e^{-b_k D_{iso}}$, with $D_{iso}$ being the diffusivity of free water.

In a particular case of the multi-fascicle model called the "ball-and-stick" model, each individual fascicle is represented by a stick in the expression of $S_{k,j}^{single\_fascile}$. With this simplification, an essential advantage of multi-fascicle models is lost: the ball-and-stick model provides information only about the fascicles orientation, but does not enable the assessment of fascicle properties such as the fascicle anisotropy and diffusivity, limiting the use of the ball-and-stick model to connectivity studies.

In contrast, since an individual fascicle is generally considered to be well represented by a single tensor in DTI, a natural candidate has been to represent each fascicle by a tensor. Considering $N_f$ tensors $D=(D_1, \ldots, D_{N_f})$ representing the $N_f$ fascicles, this amounts to setting $S_{k,j}^{single\_fascile} = e^{-b_k g_k^T D_j g_k}$ leading to the so-called multi-tensor model. The multi-tensor model has the fundamental advantage over other common representations of modeling each fascicle independently. It enables the assessment of individual fascicle characteristics by computing diffusion tensor parameters for each fascicle, which enables characterization of the white-matter appearance, changes and alterations and enables comparison of diffusion characteristics between corresponding anatomical fascicles across individuals, which is of great interest for clinical applications. In addition, the full multi-tensor model estimation enables characterization of the fraction of occupancy for each fascicle, providing information about the mixing proportions and compensating for partial volume effect.

Figure 2:
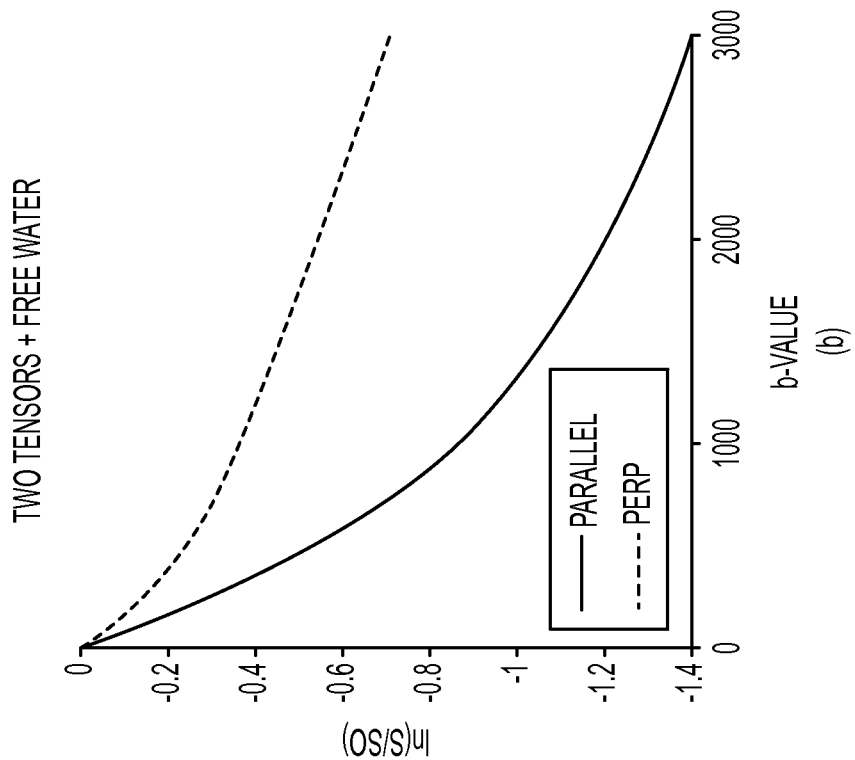
FIG. 2 illustrates the concept of non-monoexponential decay of signal with b-value detected in a voxel in a multi-fascicle model.
Figure 2:
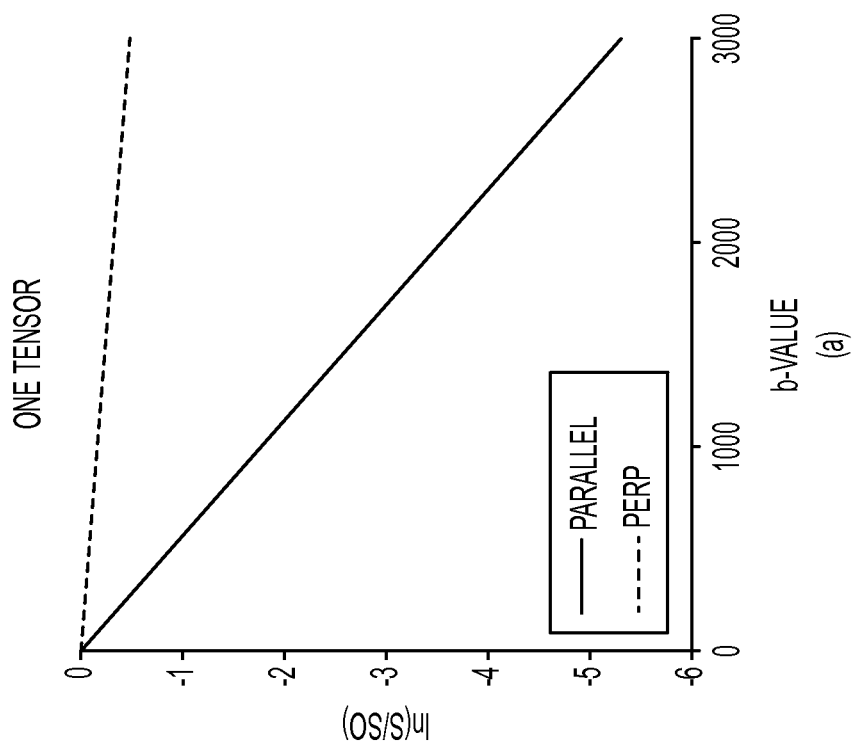

A non-monoexponential decay may be observed in voxels when imaging with high b-values, providing evidence that the single tensor model and its underlying Gaussian assumption is not appropriate to accurately represent the diffusion signal in the voxel. The biophysical mechanisms responsible for the non-monoexponential behavior are, however, numerous and not completely understood. First, it is commonly recognized that compartmentalization of the voxel in different subregions with heterogeneous properties can lead to a non-monoexponential decay under certain acquisition conditions. Particularly, as illustrated in FIG. 2, mixing of an isotropic unrestricted water compartment with multiple anisotropic compartments (e.g., see equation (2)), with each compartment being modeled with a purely monoexponential decay, leads to a non-monoexponential decay due to partial volume averaging, even at moderate b-values. At a smaller diffusion scale, the presence of intra- and extracellular compartments leads to a non-monoexponential decay for very high b-values, even for a single fascicle. Nevertheless, the presence of this phenomenon at clinically relevant b-values, with long diffusion sensitization pulse duration δ, long echo times and low signal-to-noise ratio remains unclear.

Importantly, compartmentalization is not a prerequisite for the presence of a non-monoexponential decay. The presence of a biexponential decay in the cold-injured brain parenchyma after massive membrane disintegration has been reported, and in centrifuged erythrocyte samples, non-monoexponential behavior within the intracellular space of a single cell, the frog oocyte has been observed. Other biophysical mechanisms, such as the proximity of cell membranes which locally restrict motion, and intra- and inter-cellular heterogeneities, are likely to contribute to the MR. signal decay behavior. Imaging strategies that uniquely characterize each of these properties remain under development.

FIG. 2 illustrates that intra-voxel orientation heterogeniety and partial volume averaging leads to a non-monoexponential decay in a voxel. FIG. 2A illustrates the monoexponential decay arising from a single tensor (FA=0.9, diffusivity=$2.1 \times 10^{-3}$ mm$^2$/s) as shown by the linearity of log(S/S0) in both the parallel and perpendicular directions with respect to the tensor orientation (noise-free case). FIG. 2B illustrates that mixing of an isotropic compartment ($f_0$=0.2, $D_{iso}$=$3 \times 10^{-3}$ mm$^2$/s) and two crossing fascicles represented by two single tensors ($f_1$=$f_2$=0.4, FA=0.9, diffusivity=$2.1 \times 10^{-3}$ mm$^2$/s, crossing angle=900) using equation (2) leads to a non-monoexponential decay in the voxel, even for b-values below 3000 s/mm$^2$. This illustrates that a non-monoexponential decay in a voxel may arise from a sum of mono-exponential behaviors.

Multiple approaches have been investigated to account for the non-Gaussianity of the diffusion signal in a voxel, including fitting a multi-exponential model and a "stretched-exponential model." The estimation of a Kurtosis term, which is a dimensionless measure of the deviation of the water diffusion profile from a Gaussian distribution has also been investigated. A 'composite hindered and restricted model of diffusion' (CHARMED) has been proposed, in which the diffusion signal was characterized by components arising from hindered (extra-axonal water) and restricted (intraaxonal) water diffusion, featuring a perpendicular diffusion component that is non-monoexponential. CHARMED requires long acquisition times and very high b-values (up to 10000 s/mm$^2$), limiting its use in routine clinical practice.

Most prior implementations of the above-described approaches accounting for the non-monoexponential signal decay have considered the case of a single fascicle in each voxel. For example, when estimation of a single tensor and a single Kurtosis term with b-values as low as b=2500 s/mm$^2$ was used, a significant deviation from the Gaussian distribution was measured. However, as illustrated by FIG. 2, the intra-voxel orientation heterogeneity and the partial volume effect may be the predominant sources of the observed non-monoexponential decay at such a diffusion scale. More precisely, while the presence of a non-monoexponential decay for an individual fascicle is commonly accepted when using very high b-values and a short gradient pulse duration δ, its presence in data acquired with a clinical scanner with limited b-value range and large remains unclear. Particularly, the non-monoexponential behavior may be negligible when considering b-values lower than b<3000 s/mm$^2$, and when the acquisition time or the available gradient strength is limited, a monoexponential per-fascicle model may be safely employed.

Realizing the limitations of the above-described techniques, embodiments of the present disclosure relate to a representation of each individual fascicle by a single tensor model. The full multi-tensor model estimation enables the assessment of individual fascicle characteristics in addition to the brain connectivity. Diffusion parameters (e.g., FA, MD, AD, RD) can be computed for each fascicle independently, which is of central interest for fascicle integrity assessment. The number of parameters involved is relatively small, requiring a limited number of acquisitions for their estimation. However, full multi-tensor approaches have frequently been reported to be numerically challenging and unstable, experiencing difficulties for their estimation in practice. Several of the techniques described herein demonstrate how these difficulties may be due to inappropriate imaging acquisition settings leading to an under-determined system of equations.

As discussed in more detail below, the tensors and fractions of occupancy of a multi-tensor model cannot be uniquely determined when using a single-shell HARDI acquisition. Consider a model with two fascicles represented by the two diffusion tensors $\hat{D}=(\hat{D}_1,\hat{D}_2)$ and the fractions $\hat{f}=(\hat{f}_1,1-\hat{f}_1)$, and consider an acquisition with a unique non-zero b-value b. If $(\hat{D},\hat{f})$ are the underlying true tensors and fractions, then for any $\alpha,\beta>0$ equation (2) above can be written as:

$$S_k(\hat{D}, \hat{f}) = S_0\left(\frac{\alpha}{\alpha}\hat{f}_1 e^{-bg_k^T \hat{D}_1 g_k} + \frac{\beta}{\beta}(1-\hat{f}_1)e^{-bg_k^T \hat{D}_2 g_k}\right)$$

$$= S_0\left(\alpha \hat{f}_1 e^{-bg_k^T \hat{D}_1 g_k - \log\alpha} + \beta(1-\hat{f}_1)e^{-bg_k^T \hat{D}_2 g_k - \log\beta}\right).$$

Considering $g_k^T g_k=1$, $\log \alpha = g_k^T (\log \alpha I_{3\times})g_k$, and for every gradient direction k:

$$S_k(\hat{D}, \hat{f}) = S_0\left(\alpha \hat{f}_1 e^{-bg_k^T\left(\hat{D}_1 + \frac{\log\alpha}{b}I_{3\times 3}\right)g_k} + \beta(1-\hat{f}_1)e^{-bg_k^T\left(\hat{D}_2 + \frac{\log\beta}{b}I_{3\times 3}\right)g_k}\right)$$

For $$\beta = \frac{1 - \alpha\hat{f}_1}{1 - \hat{f}_1}$$

and $\alpha \in [0,1]$, then $\beta>0$ is satisfied and so are the fundamental properties of a mixture model: (1) the fractions sum to one, i.e. $\alpha\hat{f}_1 + \beta(1-\hat{f}_1)=1$, and (2) each fraction is positive and not greater than one, i.e. $0<\alpha\hat{f}_1<1$ and $0<\beta(1-\hat{f}_1)<1$.

Consequently, when using a single non-zero b-value acquisition, then if $(\hat{f}_1, 1-\hat{f}_1)$ and $(\hat{D},\hat{f})$ are the true fractions and tensors, then for any $\kappa<\alpha\hat{f}<1$, $0<\beta(1-\hat{f}_1,1-\alpha\hat{f}_1)$ and $$\left(\hat{D}_1 + \frac{\log\alpha}{b}I_{3\times 3}, \hat{D}_2 + \frac{\log\frac{(1-\alpha\hat{f}_1)}{1-\hat{f}_1}}{b}I_{3\times 3}\right)$$

lead to the same $S_k(\hat{D},\hat{f})$ for every direction k, resulting in an infinite number of solutions. Additionally, non-degenerate tensors are obtained for $\alpha > e^{-b\lambda_1^{min}}$, $\lambda_1^{min}$ being the minimum eigenvalue of $\hat{D}_1$.

This analysis suggests that when using a single non-zero b-value, a decrease of the signal modeled by one of the tensors can be compensated by an increase of the signal modeled by the other tensor, by transforming the tensor diagonals and the fractions. In consequence, the tensor orientation is correctly estimated but the tensor size indicated by the magnitude of its eigenvalues and the partial volume fractions is not. These parameters are collinear and cannot be uniquely determined.

However, with multiple non-zero b-values $b_k$, the new tensor diagonals $$\hat{D}_1 + \frac{\log\alpha}{b_k}I_{3\times 3}$$

and $$\hat{D}_2 + \frac{\log\beta}{b_k}I_{3\times 3}$$

are functions of $b_k$. Accordingly, the use of multiple non-zero b-values enables a unique solution to be found and disambiguates the estimation of f and D, thereby allowing measurements of the fractions of occupancy and the tensor size in addition to the tensor orientation.

Consider the image domain V to be a regular 3-dimensional (3D) grid, and consider the full multi-tensor model described by:

$$S_k(D, f) = S_0\left(f_0 e^{-bD_{iso}} + \sum_{j=1}^{N_f} f_j e^{-bg_k^T D_j g_k}\right),$$

The aim is to recover the multi-tensor models $D=(D^i, i\in V)$ and the fractions $f=(f^i, i\in V)$ for each voxel of V. When estimating tensors, particular care should be taken to ensure the positive-definitive property of the $D_j$ and to avoid degenerate tensors with null or negative eigenvalues. Although such tensors are non-physical, they commonly arise in high anisotropy regions or due to noise corruption. The symmetric positive definite property of each tensor may be ensured by parameterizing the tensors in the log-Euclidean framework by setting $L^i=(L_1^i,\ldots,L_{N_f}^i)=(\log(D_1^i),\ldots,\log(D_{N_f}^i))$. This formulation ensures that tensors with null or negative eigenvalues are at an infinite distance. In contrast to Euclidean approaches, this formulation does not require any particular care to preserve tensor attributes during the computation because all operations are performed within the appropriate manifold.

Consider y to be the set of gradient images, with $y_k^i$ denoting the $i^{th}$ voxel of the gradient image k. The simultaneous estimation and regularization of f and L (and consequently D) is performed according to a maximum a posteriori principle, by maximizing.

$$\hat{L}_{MAP}, \hat{f}_{MAP} = \underset{L,f}{\arg\max}\, p(L, f \mid y) \quad (3)$$
$$= \underset{L,f}{\arg\max}\, p(y \mid L, f)p(f \mid L)p(L)$$
$$= \underset{L,f}{\arg\max}\, [\ln p(y \mid L, f) + \ln p(f \mid L) + p(L)],$$

which decomposes into a likelihood term and two prior terms. Assuming statistical independence of the noise between the images and between the voxels, so that $p(y|L, f) = \Pi_{i\in V}\Pi_{k=1}^{K} p(y_k^i|L^i, f^i)$ Furthermore, a Gaussian noise with zero-mean and variance $\sigma_k$ is assumed and the following likelihood is considered:

$$p(y_k \mid L, f) = \prod_{i\in V} \frac{1}{\sigma_k\sqrt{2\pi}} \exp\left(-\frac{\sum_{k=1}^{K}\|S_k(e^{L^i}, f^i) - y_k^i\|^2}{2\sigma_k^2}\right) \quad (4)$$

The term p(L) in equation (3) allows for incorporation of a priori knowledge on the multi-tensor field L. In accordance with some embodiments of the present disclosure, an anisotropic regularization prior that exploits spatial homogeneity but preserves sharp contours is used. More precisely, in some embodiments, smoothness of each L; by setting $p(L)=\Pi_{i\in V}\Pi_{j=1}^{N_f}\exp(-\alpha\phi\|\nabla L_j^i\|)$ where $\|L_j^i\|$ is the norm of the spatial gradient of $L_j^i$, and $\alpha$ is a parameter controlling the regularization strength is used. As generally employed, $\phi(s)=\sqrt{1+s^2/K^2}$ to account for anisotropic regularization, K being a normalization factor for the gradient. Following a one-tensor log-Euclidean model, $\|\nabla L_j^i\|^2 = \Sigma_{m-1}^3 \|\partial_{j,m}L_j^i\|_{LE}^2$ with $\|\cdot\|_{LE}$ being the log-Euclidean metric. The regularization of multiple tensor models is, however, not the straight extension of the single-tensor case. Rather, only tensors which are part of the same fascicle should be regularized together. To achieve this, an original approximation of the spatial gradient for the multiple tensor case is proposed. The partial derivative in a direction $i_m(m\in\{1,2,3\})$ is approximated by considering the two most similar neighbors $L_q^{i\pm 1_m}$ to $L_j^i$ in the following finite difference scheme:

$$\partial_{j,m}L^i \approx \frac{\arg\min_{L_q}\|L_q^{i+1_m} - L_j^i\|_{LE} - 2L_j^i + \arg\min_{L_q}\|L_q^{i-1_m} - L_j^i\|_{LE}}{2\|i_m\|} \quad (5)$$

This formulation is compatible when regularizing neighboring voxels containing a different number of tensors. A softmax approximation of the arg min operator can be considered to ensure the differentiability of the regularization term. By considering a finite set of measures $\{h(L_q)\}_q$, arg $\min_{L_q} h(L_q)$ can be approximated by:

$$\underset{L_q}{\arg\min}\, h(L_q) \approx \sum_{L_q} \omega(L_q)L_q$$

with $$\omega L_q = 1 - \frac{e^{\gamma h(L_q)}}{\sum_{L_q'} e^{\gamma h(L_q')}}.$$

This expression ensures $\omega L_q \approx 1$ for the smallest $h(L_q)$ and $\omega \approx 0$ for the others. Choosing a large value for $\gamma$ allows faster transitions of $\omega$ between 0 and 1.

In the techniques described herein, no prior knowledge on the estimated fractions was considered, and p(f|L) (see equation (3)) was considered to be a uniform density. Ultimately, by considering constant noise characteristics across acquisitions, maximization of the posterior distribution in equation (3) leads to the following minimization:

$$\hat{L}_{MAP}, \hat{f}_{MAP} = \underset{L,f}{\operatorname{argmin}} \sum_{i \in V} \sum_{k=1}^{N_g} (S_k(e^{L(x)}, f(x)) - y_k(x))^2 + \alpha \sum_{j=1}^{N_f} \phi(\|\nabla L_j(x)\|) \quad (6)$$

In some embodiments, each tensor's orientations is parameterized with the Euler angle. This representation was found to enable a more efficient optimization of the parameters. In addition, it enabled the choice of introducing various constraints to further reduce the number of parameters: symmetry of the eigenvalues (e.g., $\lambda_{11} = \lambda_{21}$), cylindrical shape of each tensor (e.g., $\lambda_{j2} = \lambda_{j3}$), bounds on the magnitude of the eigenvalues, equiplanar configuration for the tensors, and others.

In some embodiments, the model parameters are estimated by performing an iterative minimization which required a starting point. The multi-tensor fitting procedure is initialized by considering the one-tensor solution obtained by a robust least-squares estimate. The one-tensor solution may be denoted as $D_{1T} = R_{1T}^T \Lambda_{1T} R_{1T}$ with eigenvalues $\Lambda_{1T} = \operatorname{diag}(\lambda_1^{1T}, \lambda_2^{1T}, \lambda_3^{1T})$. To enable a faster convergence, the first two tensors $\exp L_1^{(0)}$ and $\exp L_2^{(0)}$ are initialized according to the rotation of $D_{1T}$ of angle $$\varphi = \pm \frac{\lambda_2^{1T}}{\lambda_1^{1T}} \frac{\pi}{4}.$$

The rotation is applied in the plane formed by the two largest eigenvalues $(\lambda_1^{1T}, \lambda_2^{1T})$ and composed with a shrink of $\lambda_2^{1T}$. In consequence, when $\lambda_1^{1T} \gg \lambda_2^{1T}$, which is likely to indicate an individual fascicle in that voxel, the initial $D_j$'s are two tensors with almost parallel principal diffusivities. In contrast, when $\lambda_1^{1T} = \lambda_2^{1T}$ the initial $D_j$'s describe two tensors whose principal diffusivities are perpendicular. When estimating more than two tensors, the orientation of $\exp L_{j \geq 3}^{(0)}$ is initialized with a random rotation of $D_{1T}$.

In accordance with some embodiments, the solution of equation (6) may be obtained using the BOBYQA algorithm described by Powell (*The BOBYQA algorithm for bound constrained optimization without derivatives. In Technical report NA2009/06. Department of Applied Mathematics and Theoretical Physics, Cambridge, England*), a recent derivative-free bound-constrained optimization technique. BOBYQA is an iterative algorithm. At each iteration, it computes from a set of points a quadratic approximation for the objective function. The point giving the largest value for the objective function is replaced by the minimum of the quadratic approximation computed in a trust region. At each iteration the trust region is updated. BOBYQA converges faster than the Newton method and enables the introduction of constraints. The introduction of constraints on the $f_j$'s enables the estimation of properly bounded fractions of occupancy ($f_j \in [0,1]$), while constraints on the Euler angles ensures the uniqueness of the Euler parameterization. It found to be less sensitive to local minima than a conjugate gradient descent scheme. The numerical optimization was achieved by considering a diffusion model with gradually increasing complexity, starting from a simple stick model and finishing by the estimation of the full multi-fascicle model including the fractions of occupancy, the tensor orientations, the tensor eigenvalues and the unrestricted water compartment. This approach made the minimization less sensitive to the initialization, providing a robust full MFM estimate at each voxel.

Illustrative Gradient Encoding Technique

As discussed above, fully estimating multi-tensor models may require the acquisition of diffusion-weighted images associated with multiple non-zero b-values. Some embodiments of the present disclosure, discussed in more detail below, are directed to a novel gradient encoding scheme, which acquires diffusion-weighted MR images that satisfy this requirement.

As discussed above, in connection with FIG. 1 and equation (1), in diffusion weighted imaging, a key parameter in controlling the signal-to-noise ratio (SNR) of the acquired data is the echo time (TE). An increase in TE results in signal dropout due to T2 relaxation and therefore results in a decrease in SNR. Selecting a gradient encoding scheme that keeps TE as low as possible facilitates the acquisition of high quality measurements. The minimum achievable TE for a gradient encoding scheme is constrained by the choice of the nominal b-value $b_{nominal} = \gamma^2 \delta^2 (\Delta - \delta/3)$ of the acquisition. The minimum achievable TE follows a complex relationship with $b_{nominal}$ which can be approximated by:

$$TE \approx \left( \frac{12 b_{nominal}}{\gamma^2} \right)^{1/3} \quad (7)$$

An ideal acquisition scheme for the estimation of a full multi-tensor model should (1) achieve multiple non-zero b-values and (2) achieve an optimal trade-off between imaging high b-values and minimizing the TE to maximize the SNR.

As described above, some conventional techniques for estimating a multi-tensor model employ diffusion-weighted data acquired using a single-shell HARDI acquisition scheme, which specifies gradients of constant strength $\|g_k\| = 1$ for each direction and provides a single-radius spherical sampling in q-space. Because the applied b-value is $b_{nominal} \|g_k\|^2$, a single-shell HARDI acquires only a single non-zero b-value equal to $b_{nominal}$, which, for at least the reasons discussed above (e.g., see FIG. 2), is not suited for the full estimation of multiple tensors. Separate HARDI scans with different nominal b-values can be employed to image multiple non-zero b-values. However, modifying the nominal b-value for the separate HARDI scans results in a different TE for each scan (e.g., see equation (7)). Having different TE values for different scans causes different signal dropout artifacts between the scans and potentially different eddy current distortion, making the alignment of the corresponding DW images challenging and perturbing the diffusion model estimation. Additionally, acquisition of several separate single-shell HARDI scans is more prone to patient motion between the scans.

Multi-shell HARDI combines in a single acquisition the sampling of multiple spheres in q-space by modulation of $b_{nominal}$ with various gradient strengths $\|g_k\| \leq 1$. Because the unit-norm gradients $\|g_k\| = 1$ correspond to the shell of largest radius, the nominal b-value for a multi-shell HARDI is set based on the highest b-value of the acquisition. Since imaging of high b-values (e.g., 2000 s/mm² or more) is known to provide a better separation of multiple fascicles and to facilitate the estimation of their orientation, a multi-shell HARDI with a high nominal b-value is typically preferred. A undesirable aspect of this approach, however, is a substantially increased TE when compared with a single-shell HARDI acquisition. The increased TE for multi-shell HARDI results in an increased acquisition time and a lower signal-to-noise ratio for all the measurements (e.g., see equation (1)), impacting both the low and the high b-value measurements. Additionally, imaging a higher nominal b-value is generally achieved by using longer diffusion gradient pulses, which in turn leads to larger eddy current distortion.

Some embodiments in accordance with the present disclosure relate to a novel technique (referred to herein as CUbe and SPhere or "CUSP") for acquiring diffusion-weighted images associated with multiple non-zero b-values. Multiple non-zero b-values are acquired by combining a first set of gradients for a single-shell HARDI acquisition at a specified $b_{nominal}$ (e.g., 1000 s/mm²) with a second set of gradients having one or more different b-values and having associated gradient strengths that cause the gradients to lie within an enclosing cube of the inner shell. For example, the first set of gradients for the single-shell HARDI may uniformly sample the diffusion signal on the hemisphere, which is described by unit-norm gradients $\|g_k\|=1$. This inner shell employs the b-value providing the desired "optimal" SNR for the diffusion weighted acquisition.

In some embodiments, the b-value for the inner shell may be determined by $b_{optimal}=1.11/\text{ADC}$, where ADC is the apparent diffusion coefficient of the tissue being imaged. An illustrative, non-limiting value for specified $b_{nominal}=b_{optimal}=1000$ s/mm² for an adult brain and $b_{optimal}=800$ s/mm² for a pediatric brain. The single-shell HARDI provides a full spherical sampling with the desired SNR and TE for the b-value $b_{nominal}$. A second set of gradient vectors may be specified to acquire additional b-values $b_k=b_{nominal}\|g_k\|^2$ without modifying the TE by modulation of $b_{nominal}$ with gradients whose strengths are greater than one: $\|g_k\|>1$.

In some embodiments, the only constraint for $g_k$ is to have unit norm components, corresponding to the normalized current intensity in each gradient coil. Denoting the gradient components by $g_k=[g_k^X, g_k^Y, g_k^Z]^T$, this leads to $|g_k^X| \leq |g_k^Y| \leq |g_k^Z| \leq 1$, which describes the enclosing cube of the sphere of radius $\|g_k\|=1$, which is also referred to herein as the "cube of constant TE." Any gradient in this region can be acquired without modifying the TE by selecting the appropriate gradient strength. Because the diffusion sensitivity is dependent on the square of the gradient norm, imaging in the cube of constant TE enables the acquisition of b-values up to $3b_{nominal}$. This maximum b-value is obtained when using the four non-symmetric 0-norm tetrahedral gradients extending to the corners of the cube of constant TE($|g_k^X|=|g_k^Y|=|g_k^Z|=1$).

Figure 3:
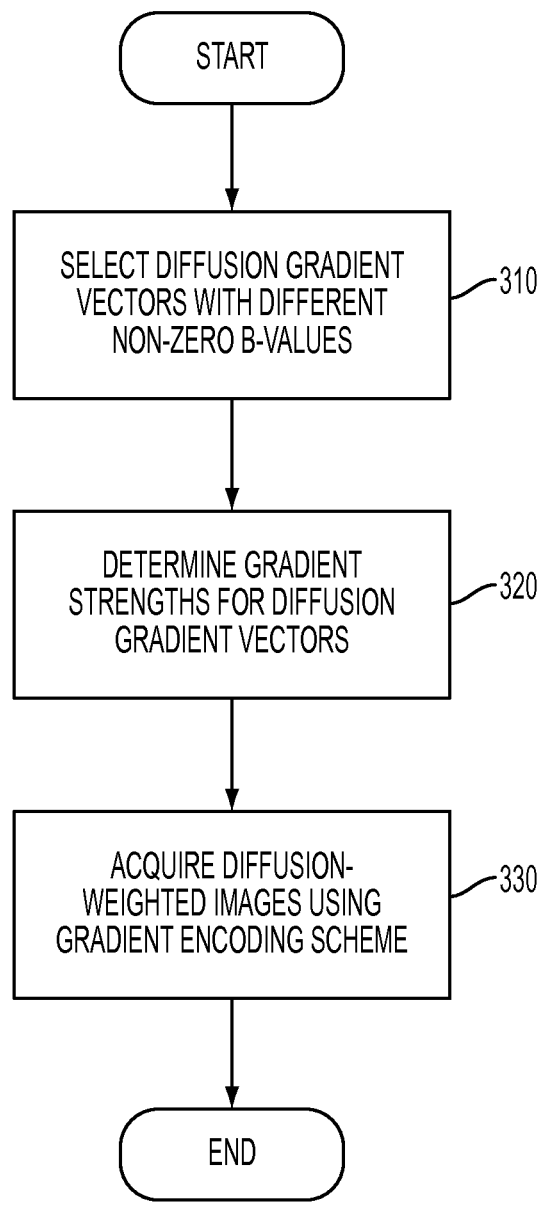
FIG. 3 illustrates a process for determining a gradient encoding scheme for acquiring diffusion-weighted images with multiple b-values in accordance with some embodiments.

FIG. 3 shows an illustrative process for determining a gradient encoding scheme for diffusion-weighted magnetic resonance imaging in accordance with some embodiments of the present disclosure. In act 310, diffusion gradient vectors are selected, wherein at least two of the diffusion gradient vectors are associated with different non-zero b-values. For example, as discussed in more detail below, the diffusion gradient vectors for the gradient encoding scheme may include a first set of diffusion gradient vectors corresponding to a single-shell HARDI acquisition each having a b-value of $b_{nominal}$ and a second set (e.g., one or more) of diffusion gradient vectors each being associated a b-value different than $b_{nominal}$.

The process then proceeds to act 320, where the gradient strengths for each of the diffusion gradient vectors is determined. As discussed above, in some embodiments, the plurality of diffusion vectors in the gradient encoding scheme may include a first set of diffusion gradient vectors corresponding to a single-shell HARDI acquisition. Each of the gradient vectors in the first set may have an identical gradient strength $\|g_k\|=1$ as they all fall on the surface of the sphere having a radius that corresponds to $b_{nominal}$. In contrast, the gradient strengths of the gradient vectors in the second set may be determined in any suitable way, with the only constraint that all of the vectors in the second set fall on or inside of the cube of constant TE. Illustrative techniques for selecting the gradient strength of vectors in the second set in accordance with some embodiments of the present disclosure are discussed in more detail below.

Having defined all of the gradient orientations and gradient strengths in the gradient encoding scheme, the process then proceeds to act 330, where the gradient encoding scheme is used to acquire diffusion-weighted measurements. For example, an MRI system may be programmed with the determined gradient encoding scheme to control various components of the device to acquire diffusion-weighted images having multiple non-zero b-values. The diffusion-weighted measurements may then be used to approximate one or more diffusion-based parameters in a multi-tensor model, as described above. Illustrative experiments using some of the techniques described herein for acquiring diffusion-weighted measurements with multiple non-zero b-values are discussed in more detail below.

As discussed above, some embodiments for acquiring diffusion-weighted images in accordance with the techniques described herein may employ any suitable acquisition technique that acquires multiple non-zero b-values without increasing TE beyond the TE of a single-shell HARDI acquisition. That is, the gradient vectors in the single-shell HARDI acquisition may set the maximum allowable TE for the gradient encoding scheme, and all gradient vectors included in the acquisition may be associated with b-values that result in a corresponding TE being equal to or less than the maximum allowable TE set by the single-shell HARDI.

Figure 4:
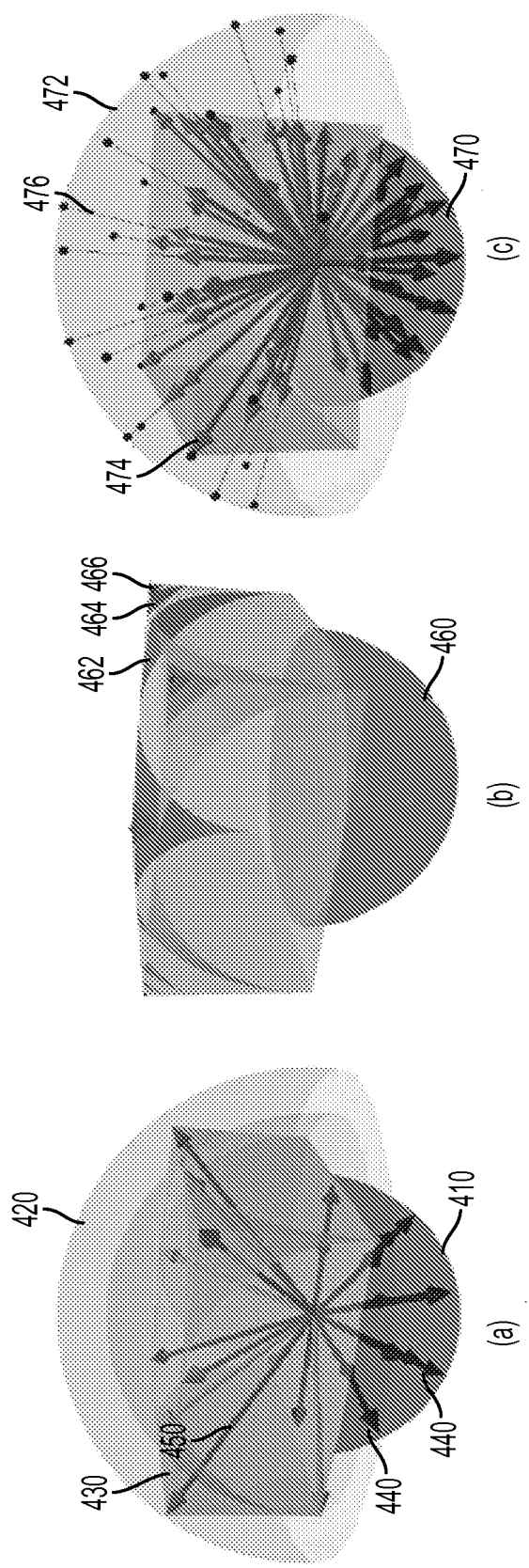
FIG. 4 schematically illustrates three techniques (FIG. 4A: CUSP-T.

In some embodiments, a gradient encoding scheme used to acquire diffusion-weighted images in accordance with the present disclosure is defined based, at least in part, on a generalization of a multi-shell HARDI. FIG. 4A illustrates a first technique (also called "CUSP-Truncated" or "CUSP-T" herein) that considers a conventional multi-shell HARDI composed of K>2 shells and truncates those parts of the shells that project outside the cube of constant TE of the inner shell. As shown in FIG. 4A, in this acquisition scheme, an inner shell 410 and at least one outer shell 420 having a radius larger than that of the inner shell 410 are defined. A cube of constant TE 430 is defined as the cube that encloses the inner shell 410. A first set of diffusion gradient vectors (e.g., including gradient vectors 440), having orientations distributed (e.g, uniformly distributed) on the surface of the inner shell 410, and corresponding to a single-shell HARDI are defined. A second set of gradient vectors (e.g., including gradient vector 450) having orientations distributed on the surface of the outer shell 420, and the gradient strengths of the vectors in the second set may be reduced (e.g., by truncating the outer shell) to fall within the cube of constant TE 430 as illustrated in FIG. 4A. More generally, in the CUSP-T acquisition scheme, multiple (K≥2) uniformly spaced shells with b-values distributed across the cube of constant TE 430 may be employed. For example, in some embodiments, three shells corresponding to different b-values may be created and the two outer shells may be truncated to the cube of constant TE. Any suitable number and orientation of gradient vectors associated with each of the shell may be used, and embodiments of the present disclosure are not limited in this respect.

Because the signal strength varies as $S_k(D) = S_0 e^{-TE/T2} e^{-b_k g_k^T D g_k}$ and the SNR exponentially decreases with increasing b-value $b_k$, a second illustrative acquisition scheme (also called "CUSP-eXponential Truncated" or "CUSP-xT" herein) employs multiple shells with exponential spacing as illustrated in FIG. 4B. In particular, FIG. 4B shows four exponentially-spaced shells which have been truncated to the cube of constant TE enclosing the inner shell 460. As should be apparent from FIG. 4B, the distance between inner shell 460 and the truncated outer shells 462, 464, and 466 is an exponential spacing such that the distance between the outer shells is less than the distance between in the inner shells. Using the CUSP-xT technique, the obtained exponentially increasing shell density with increasing b-value counter-balances the loss in SNR by sampling q-space in a manner that achieves an improved uniformity of SNR.

Although only uniform spacing and exponential spacing of the multiple shells has been described, it should be appreciated that any suitable spacing between shells may alternatively be used, and embodiments of the present disclosure are not limited in this respect.

FIG. 4C schematically illustrates another illustrative acquisition scheme (called CUSP-Projection or CUSP-P) composed of an inner shell 470 at $b_{nominal}$ and an outer shell 472 at $3b_{nominal}$. The outer shell 472 passes exactly through the corners of the cube of constant TE such that the gradient vectors located at the corners (e.g., gradient vector 474) are located both on the surface of outer shell 472 and on the cube of constant TE. Other gradient vectors on the surface of the outer shell 472 (e.g., gradient vector 476) are outside of the cube of constant TE and cannot be imaged without modifying the TE. Such vectors are projected onto the faces of the cube of constant TE as shown in FIG. 4C. This technique provides high angular resolution imaging with a large number of different b-values above $b_{nominal}$ without any additional cost in TE.

Although only three illustrative techniques have been described above for selecting gradients in a gradient encoding scheme, any suitable technique may be used to select gradients in the gradient encoding scheme to, for example, identify maximally isotropic subsets of gradient orientations between the shells. Furthermore, if desired, certain gradient directions can be fixed on each shell or one or more of the gradient directions may vary on the different shells.

In some embodiments, less than all of the gradient vectors in a second set of gradient vectors (e.g., the gradient vectors not corresponding to the single-shell HARDI) may have gradient strengths that extend the gradient vectors to the faces of the cube of constant TE. For example, at least some of the gradient strengths for the gradient vectors in the second set may be selected such that the corresponding gradient vector is located between the outside of the inner shell and the inside of the cube of constant TE. In yet other embodiments, at least some of the gradient strengths may be selected such that the corresponding gradient vector is located inside of the inner shell. That is, although the bounds of the cube of constant TE may set a maximum TE value, in some embodiments, gradient vectors may be included in the gradient encoding scheme that are associated with smaller TE values than the maximum TE. Furthermore, any combination of orientation and gradient strength may be selected for gradients in the gradient encoding scheme to achieve gradients with desired b-values, with the only constraint being that all diffusion gradient vectors be located within the cube of constant TE.

The diffusion-weighted acquisition techniques described herein enable the full estimation of a multiple fascicle model. A particular strength of the techniques is to provide multiple non-zero b-values, and higher b-values than the nominal b-value, while achieving the same low TE as a single-shell HARDI. Consequently, these techniques do not increase the imaging time, increase the eddy current distortion, and they provides an improved signal-to-noise ratio for all the measurements when compared to prior multi-shell HARDI techniques.

The discussion above provides a theoretical demonstration that only the tensor orientation can be uniquely estimated when using diffusion-weighted measurements corresponding to a single non-zero b-value. Multiple non-zero b-values are required to fully estimate the tensors' direction in addition to the tensors' size and their respective fraction of occupancy. An optimization algorithm for the estimation of the parameters of a multi-fascicle model (MFM) formulated as a log-Euclidean Maximum A Posteriori estimation problem is also described above. This algorithm estimates non-degenerate tensors and incorporates a finite difference spatial regularization scheme. To acquire diffusion-weighted measurements that include multiple non-zero b-values, but without increasing TE above that needed for a single-shell HARDI, novel CUSP acquisition techniques have been described based, at least in part, on a generalization of a multi-shell HARDI. The CUSP techniques satisfy the requirement of multiple non-zero b-values and incorporate b-values larger than $b_{nominal}$ while employing the same minimum achievable TE as a single-shell acquisition. Consequently, the imaging time and the eddy current distortion are not increased. Compared to a multi-shell HARDI, the CUSP acquisition techniques achieve a better SNR. The performance and properties of CUSP-MFM techniques in accordance with some embodiments of the present disclosure are investigated through several experiments described in more detail below.

Illustrative MFM Estimation Algorithm

A multi-tensor estimation algorithm (called CUSP-MFM herein) was implemented in C++ and parallelized over the image space. The model parameters were set as follows. The diffusivity of free water at 37° C. was set to $D_{iso} = 3.0 \times 10^{-3}$ mm$^2$/s. The anisotropic regularization parameter K was set to 0.01 and the regularization influence parameter a progressively increased between $[0, \alpha_{max} = 1]$, playing the role of the inverse of a decreasing temperature. This allows to first explore a larger number of solutions (high temperature) and in a second step to constrain the solution by gradually increasing the weight of the neighborhood (low temperature). Since the minimization was performed with the BOBYQA algorithm, which is a derivative-free optimization technique, the original argmin operator in equation (5) and not its softmax approximation was used. As discussed further below, a maximum of $N_f = 2$ or $N_f = 3$ tensors per voxel were considered. The isotropic water fraction was initialized to $f_0^{(0)} = 0.1$, and the fascicle fractions to $f_j^{(0)} = 0.9/N_f$ for $j \in 1, \ldots, N_f$. All parameters may be estimated simultaneously with CUSP-MFM. However, in order to reduce the number of parameters, each tensor was constrained to have a cylindrical shape by setting $\lambda_{j,2}=\lambda_{j,3}$ for $j \in 1, \ldots, N_f$. A cylindrical shape was also employed and is generally considered reasonable with regard to the expected shape of a fascicle. Consequently, fitting the multi-fascicle model involved estimating $5N_f$ free parameters: four parameters per tensor, and $N_f$ parameters for the $N_f+1$ fractions. Model order selection was used to determine the number of fascicles at each voxel when appropriate using the F-test method. A number of other model selection approaches would also be readily apparent to those of skill in the art.

Illustrative Experiment 1: Two-Tensor Synthetic Data

Various synthetic phantoms were generated to evaluate CUSP-MFM. The tensor profile $D_j$ representing an individual fascicle was chosen to match typical in vivo data observations. A trace of $Tr(D_j)=2.1\times10^{-3}$ mm²/s was chosen, FA varied for each tensor ($FA_1=0.9$; $FA_2=0.7$) was simulated. The fractions for the isotropic compartment ($f_0$) and the tensors ($f_1,f_2$) were set to ($f_0,f_1,f_2$)=(0.15, 0.6, 0.25). The diffusion-weighted signal was simulated for different acquisition schemes and corrupted by various Rician-noise levels. The reported SNR was computed on the b=0 s/mm² images.

The short duration acquisitions with a low number of directions which are of practical interest for clinical applications were focused on. A CUSP-T acquisition consisting of a total of thirty-five images, referred to as CUSP35, was used. CUSP35 was constructed from a truncated three-shells HARDI composed of five b=0 s/mm², an inner shell of sixteen directions at b=1000 s/mm², a second shell at $b_2=2000$ s/mm² and a third shell at $b_3=3000$ s/mm² The gradients of the inner shell were uniformly distributed on the hemisphere by minimizing the sum of the electrostatic repulsive forces. The second shell was truncated to the cube of constant TE by imaging the six hexahedral gradients which are located at the intersection of the second shell and the edges of the cube of constant TE. The truncation of the third shell to the cube of constant TE led to four b=3000 s/mm² tetrahedral gradients. Two repetitions of the b=3000 s/mm² gradients were used to counterbalance the lower SNR associated with such high b-value measurements.

The CUSP35 acquisition scheme was compared to a single-shell HARDI acquisition, referred to as HARDI35, which includes five b=0 s/mm² images and one shell of thirty directions at b=1000 s/mm². An acquisition scheme with five b=0 s/mm² and 251 unique directions (HARDI256) was also considered. An electrostatic repulsion algorithm of was applied to determine uniformly distributed gradient orientations on the hemisphere for both the HARDI35 and HARDI256 acquisitions. In the following discussion, HARDI35-MFM and CUSP35-MFM refers to the MFM estimation performed by the MFM technique described herein with respectively the HARDI35 and the CUSP35 acquisition schemes. Identical estimation parameters were employed in HARDI35-MFM and CUSP35-MFM.

For each experiment both qualitative and quantitative results are reported. For the quantitative analysis, the estimated multi-fascicle model was compared to the synthetic ground truth using different metrics. The tensors were compared in term of average log-Euclidean distance (tALED), taking into account a possible permutation between the estimated and the reference tensors:

$$tALED(D^a,D^b)=\min(\|D_1^a-D_1^b\|_{LE}+\|D_2^a-D_2^b\|_{LE},$$
$$\|D_1^a-D_2^b\|_{LE}+\|D_2^a-D_1^b\|_{LE}).$$

Using the log-Euclidean metric enabled a full comparison of the tensors rather than just the crossing angle as frequently done in the literature. The corresponding fractions were compared in terms of average absolute difference (fAAD). The multi-fascicle model was also compared to the previously-described ball and stick model implemented in FSL. Since the ball and stick model estimates only the fascicle orientations it was not possible to compare the full tensors nor to compare diffusion scalar parameters. Consequently the fitting algorithm described herein was compared to the ball-and-stick algorithm by assessing the average minimum angle (tAMA) widely used in the literature. Finally, the diffusion signal arising from two uniform crossing fascicles was simulated for various Rician noise corruption levels (50 dB and 30 dB). MFM estimation was then carried out and the uniformity of diffusion scalar parameters along the fascicles was characterized.

As illustrated in FIG. 5A, a set of phantoms containing one hundred two-tensor models separated by a given angle with various orientations was generated. Ten phantoms with crossing angles from 0 to 900 were generated. FIGS. 5B and 5C qualitatively show the improvement when estimating the tensors from the CUSP35 acquisition (FIG. 5B) compared to a single-shell HARDI35 acquisition (FIG. 5C). In particular, as shown, both the tensors and the fraction $f_1$ are more uniform with CUSP35-MFM compared to HARDI35.

Figure 6:
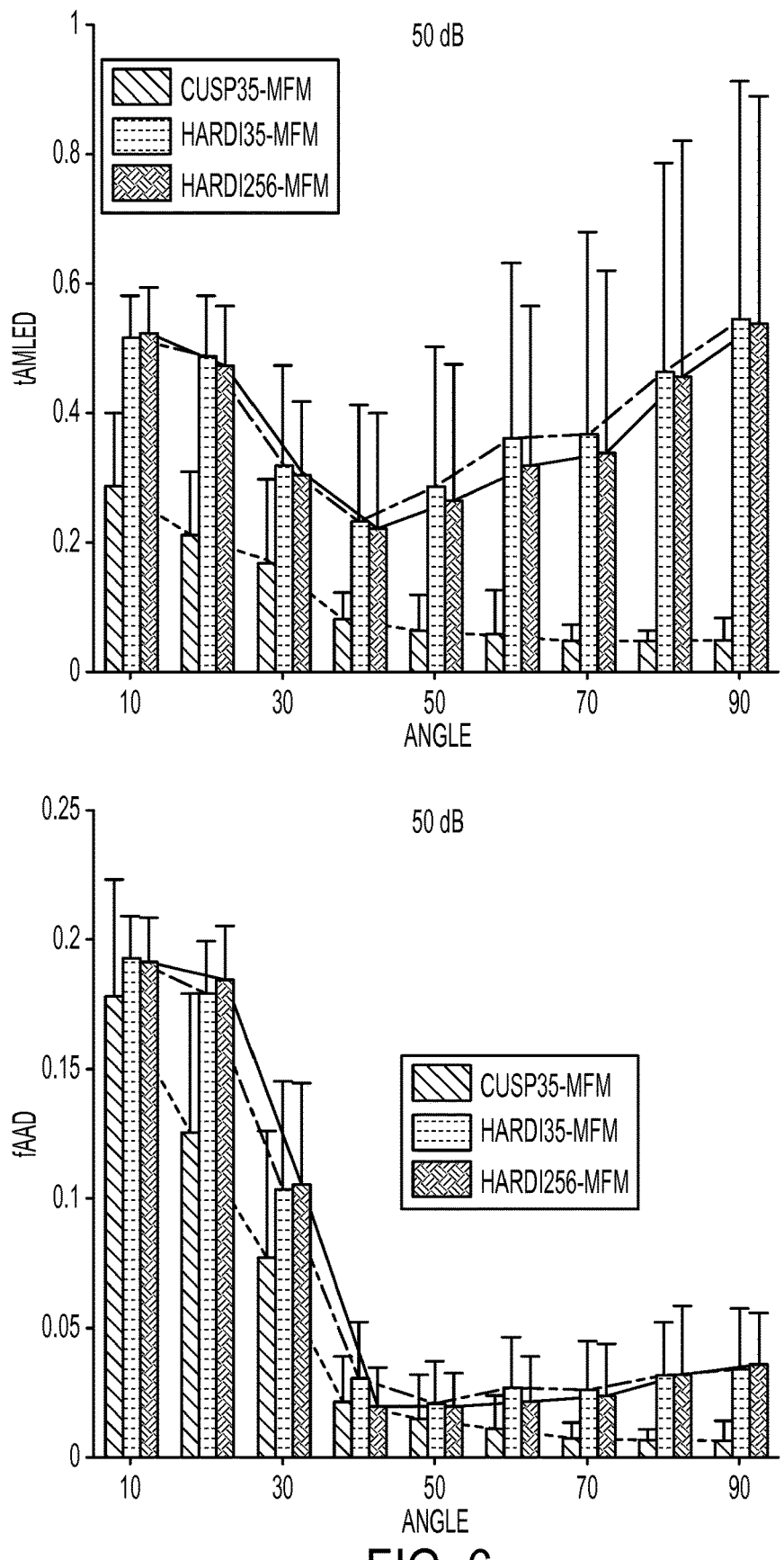
FIG. 6 shows a quantitative evaluation of the CUSP-MFM technique used in accordance with some embodiments.
Figure 6:
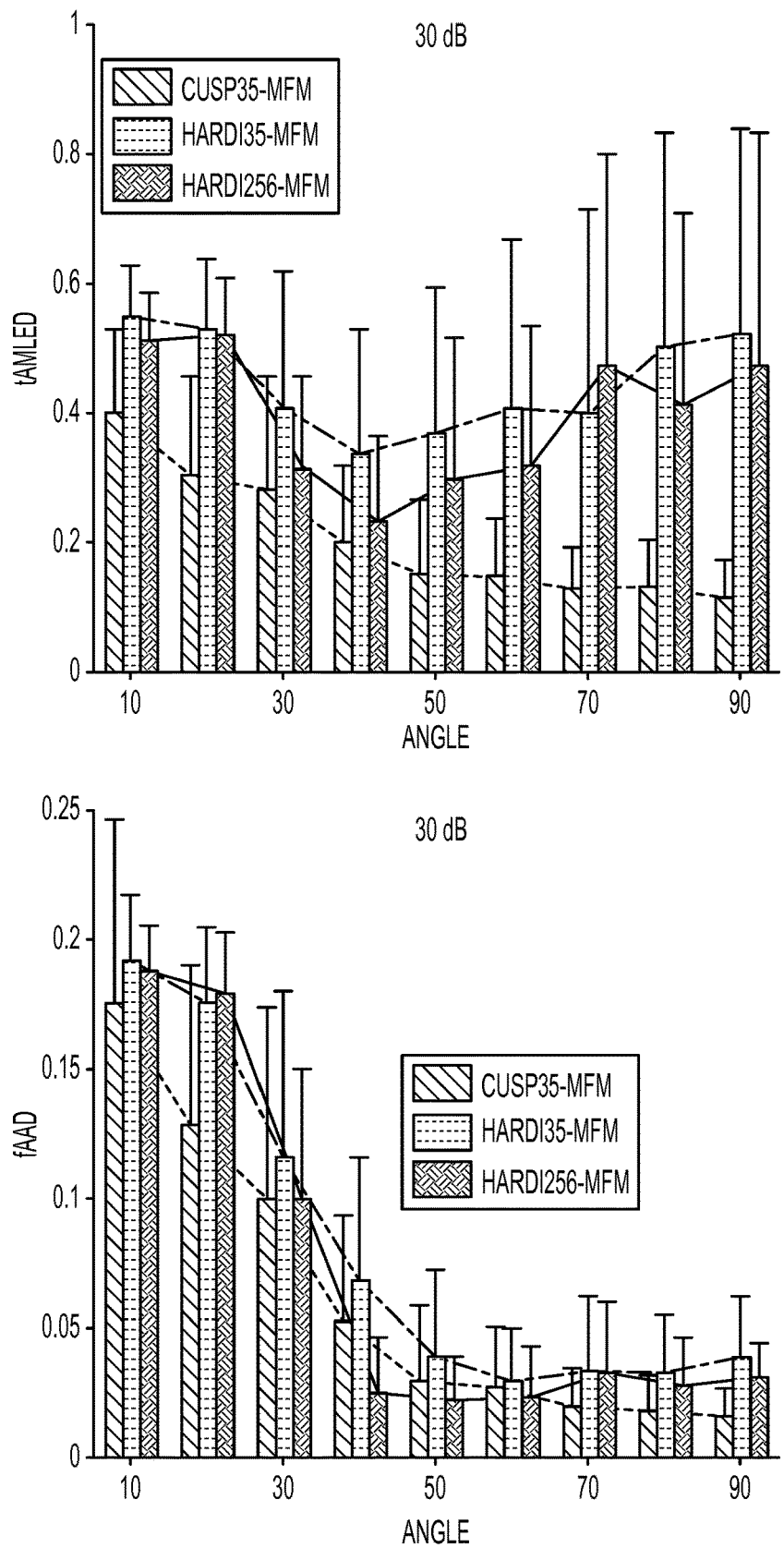

FIG. 6 quantitatively reports the estimation accuracy for various SNR (50 dB, 30 dB). For each angle (from 0° to 90°) the mean and variance of the tALED and fAAD metrics over the one hundred tensors are shown. In particular, FIG. 6 shows the CUSP35 encoding scheme achieves better results than HARDI35 and HARDI256. Accordingly, it experimentally supports the theoretical demonstration above that multiple non-zero b-values are required to fully estimate the tensors. In fact, even employing up to 251 unique directions (HARDI256) does not dramatically improve the results since it does not solve the problem that the parameters are collinear.

Figure 7:
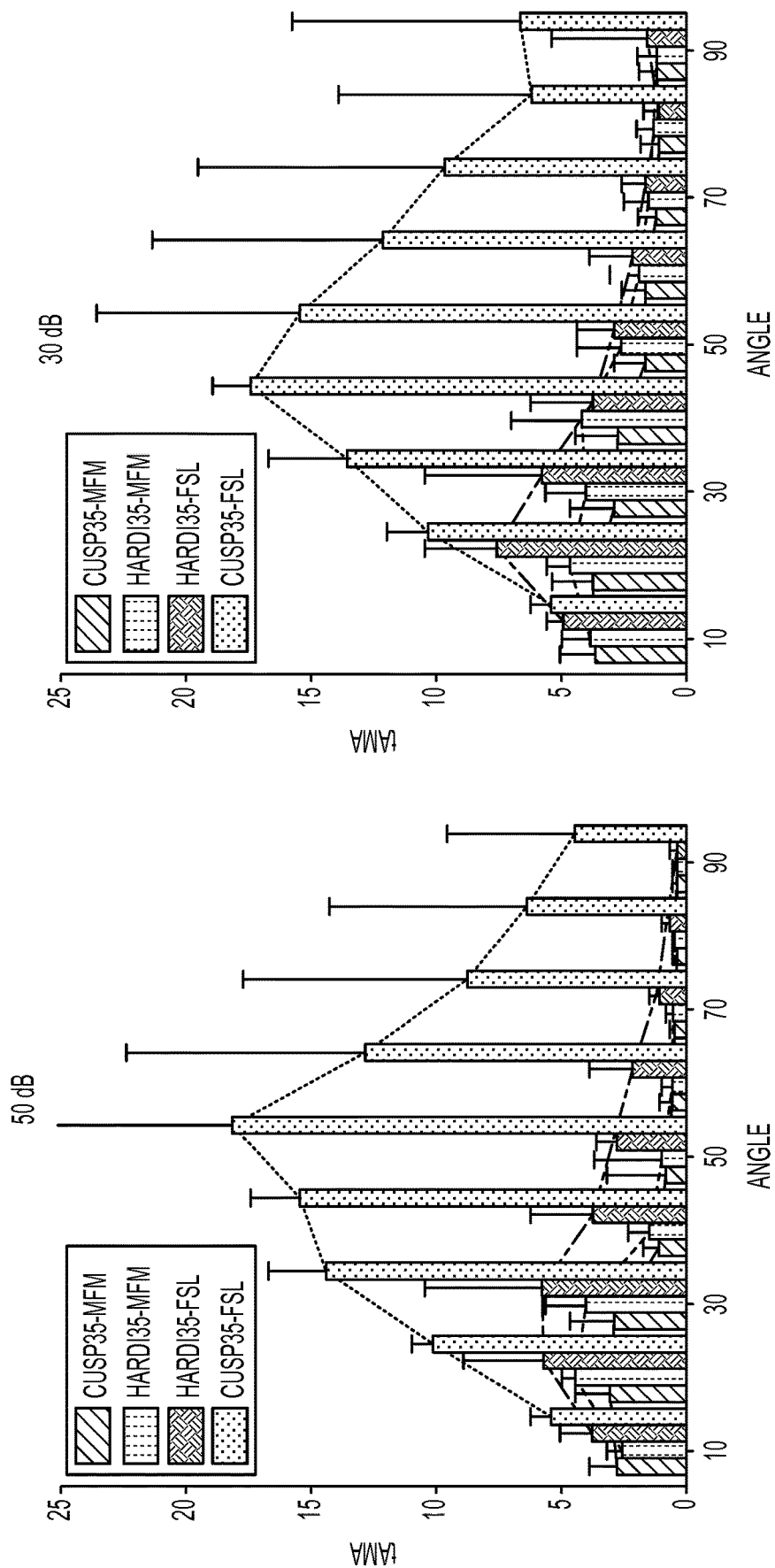
FIG. 7 shows a quantitative evaluation of the angle detection accuracy for the CUSP-MFM technique used in accordance with some embodiments.

FIG. 7 shows a comparison of the MFM algorithm to the ball-and-stick algorithm implemented in FSL. FSL does not perform well with the CUSP35 acquisition scheme. The CUSP35-MFM technique provides the best angular resolution compared to the other approaches, particularly for small angles, while this technique provides more information by estimating the full tensors. With CUSP-MFM, each fascicle can be characterized by evaluating the diffusion tensor parameters (FA, MD, etc.) of each tensor.

Figure 8:
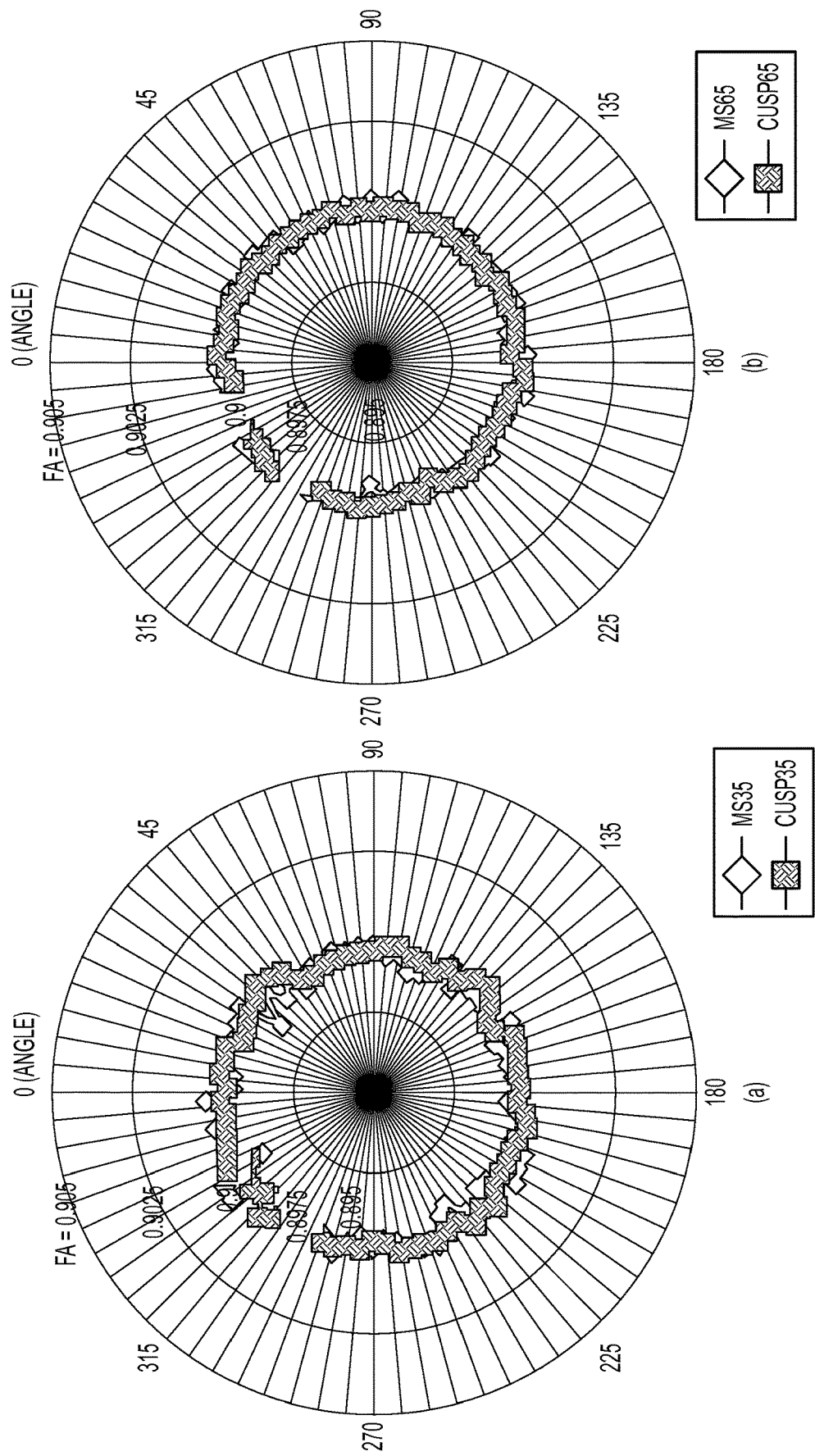
FIG. 8 shows a comparison of the angular dependency for various acquisition schemes in accordance with some embodiments.

Additionally, it was determined whether or not CUSP introduces an angular preference for certain spatial directions when characterizing fascicles (FIG. 8). Diffusion-weighted images were simulated for a single tensor with constant FA (FA=0.9) with various orientations, for both the CUSP and the multi-shell HARDI acquisitions. The tensor was rotated around its third eigenvector by increments of five degrees between 0 and 360 degrees. For each orientation, the tensor representing the fascicle was estimated, and its FA assessed. This was repeated one hundred times. FIG. 8 shows the mean FA for each tensor orientation over the one hundred repetitions. The mean FA obtained with a multi-shell HARDI and with CUSP are comparable, showing that such a multi-shell HARDI and CUSP have a uniform angular sensitivity to fascicle orientation.

A phantom representing two uniform fascicles ($FA_1=0.9$; $FA_2=0.7$) crossing with an angle of 60' was generated (see FIG. 9). In this experiment, the F-test model selection was used. The resulting multi-tensor field is reported in FIG. 9A.

It shows more uniform tensors when using CUSP35-MFM compared to HARDI35-MFM.

FIG. 9B reports the estimated fraction $f_0$ of the isotropic diffusion compartment. It shows that CUSP35-MFM provides an estimate of $f_0$ very close to the true simulated value (0.15), while the isotropic water fraction cannot be accurately estimated with HARDI35-MFM. Finally, FIG. 9C depicts the FA (non)uniformity along the fascicles. For illustration, the z-coordinate of the tract streamlines was modified to encode for the FA along the tract. It shows that CUSP35-MFM provides a much more uniform FA than HARDI35-MFM.

Figure 10:
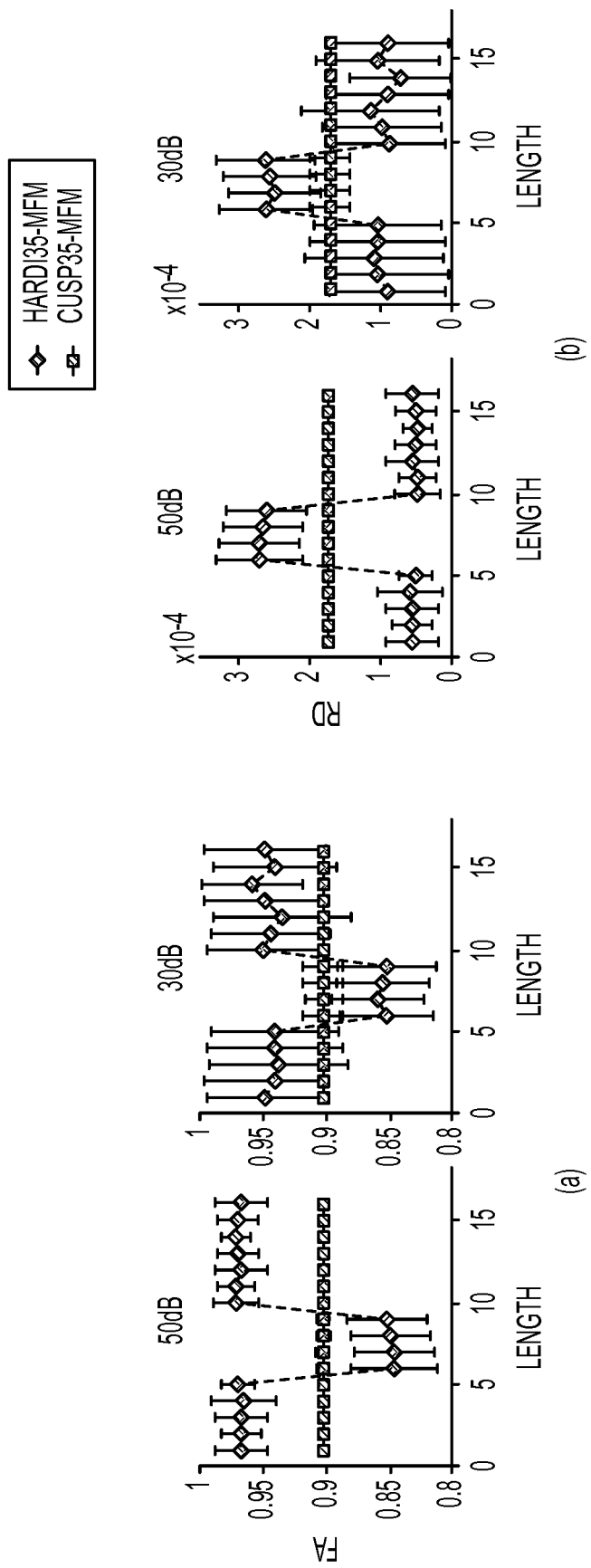
FIG. 10 shows a quantitative evaluation of fascicle characteristics along a uniform fascicle for the CUSP-MFM technique used in accordance with some embodiments.

These findings were quantitatively verified by simulating one hundred times the diffusion signal for different signal-to-noise ratios (50 dB and 30 dB). FIG. 10 reports the mean and variance of the FA (FIG. 10A) and of the radial diffusivity (RD) (FIG. 10B) over these experiments. With CUSP35-MFM, the FA and the RD of two uniform fascicles is distinctly more uniform than with HARDI35-MFM, which is highly relevant to accurately characterize the fascicles.

Illustrative Experiment 2: In Vivo Data

The performance of CUSP-MFM was assessed on in vivo data acquired on a Siemens 3T Trio scanner with a 32 channel head coil. The scanned subjects were all healthy volunteers, of age between 28 and 30 years old. The acquisition parameters used were as follows: 66 slices, FOV=215 mm, matrix=120×120, resolution=1.8×1.8×2.4 mm³ Eddy current distortion was minimized by utilizing a twice-refocused spin echo sequence. In initial experiments, the same gradient strength and orientation as those used in the synthetic experiments (CUSP35 and HARDI35) described above, were used. The minimum achievable TE/TR for both CUSP35 and HARDI35 were identical and equal to TE=86 ms/TR=9500 ms, achieving an acquisition duration of less than six minutes.

A multi-shell HARDI composed of 5 b=0 s/mm² and three shells of 20 gradient directions each at b=1000 s/mm², b=2000 s/mm² and b=3000 s/mm², referred to as MSHARDI-65. Maximally isotropic gradient subsets were obtained.

A CUSP-P acquisition referred to as CUSP65 was acquired and constructed from a projected two-shell HARDI (FIG. 4C) consisting of 5 b=0 s/mm² images, 30 gradients on the inner shell at b=1000 s/mm² and 30 gradients on the outer shell at b=3000 s/mm². A generalization of the optimization algorithm of Cook et. al (2007) "*Optimal acquisition orders of diffusion weighted MRI measurements*" *J Magn Reson Imaging* 25: 1051-1058 was used to determine maximally isotropic gradient subsets for the CUSP-P acquisition. More precisely, first the subset of 30 gradients of the inner shell was optimized using an electrostatic repulsion model, providing uniformly distributed gradient directions on the hemisphere. Then the second subset of 30 gradients was optimized with the electrostatic repulsion model while (1) taking into account the repulsion in orientation with the first subset and (2) enforcing the inclusion of gradients at b=2000 s/mm² and b=3000 s/mm² to ensure that high b-value images were acquired and for comparison to the multi-shell HARDI. The gradients of this second shell were projected to the cube of constant TE to avoid any increase in TE (see FIG. 4C) compared to imaging the inner shell only. The TE for MSHARDI-65 and CUSP-65 was respectively 108 ms and 78 ms, and the acquisition time was less than twelve minutes.

Additionally, a T1-weighted MPRAGE image was acquired with the following parameters: 160 slices, FOV=205 mm, matrix=256×256, resolution=0.8×0.8×1 mm³, TE=2.27 ms, TR=1410 ms, 3 min 50 sec. This anatomical scan was used to visualize the results.

The diffusion weighted images were corrected for head motion during the scan by rigid registration of the DW-images to the b=0 s/mm² image. The gradient orientations were compensated for the rotation component of the transformation for each image. The estimation of $N_f=2$ and $N_f=3$ fascicles was considered, with and without employing the F-test model selection. The multi-fascicle model estimation time was approximately 1 hour and 30 minutes for $N_f=2$ and 2 hours for $N_f=3$ on a 8 Core 3 Ghz Intel Xeon processor. The $N_f=2$ fascicles case was compared with the above-described ball-and-stick model implemented in FSL. The ball-and-stick model after noise correction of the DW images was also compared with a Joint Linear Minimum Mean Squared Error (LMMSE) filter.

An experiment was performed to examine the effect of CUSP-MFM on the assessment of tensor diffusion parameters. Twenty random rotations were applied to both the in vivo CUSP35 and HARDI35 acquisitions. This simulated variations of the partial volume effect in each voxel, and consequently variations of the partial volume fractions of each tensor in each voxel. However, the fractional anisotropy should be stable across the rotations. A fascicle of the corticospinal tract was selected and the fraction anisotropy was assessed along this same tract for the multiple rotations. The results were compared when using CUSP and the single-shell HARDI.

Finally, a quantitative comparison of CUSP to a multi-shell HARDI was achieved by assessing the estimation uncertainty via residual bootstrapping. The residual bootstrap is a model-based resampling technique, which is based on the estimation of a model (here the multi-fascicle model) and on the generation of a set of virtual new DWI acquisitions by randomly sampling the model residuals. In contrast to repetition-based resampling techniques, the residual bootstrap technique does not require any repetition of the gradient directions during the acquisition. Contrary to the wild bootstrap, the residual bootstrap technique does not assume any symmetry in the distribution of the residuals. The residual bootstrap has been shown to lead to smaller biases and reduced overall errors in comparison to the wild bootstrap, enabling the estimation of uncertainties with higher accuracy. In these experiments, the residual bootstrap method was employed to quantitatively compare the estimation uncertainty with CUSP-65 and with MSHARDI-65.

Figure 11:
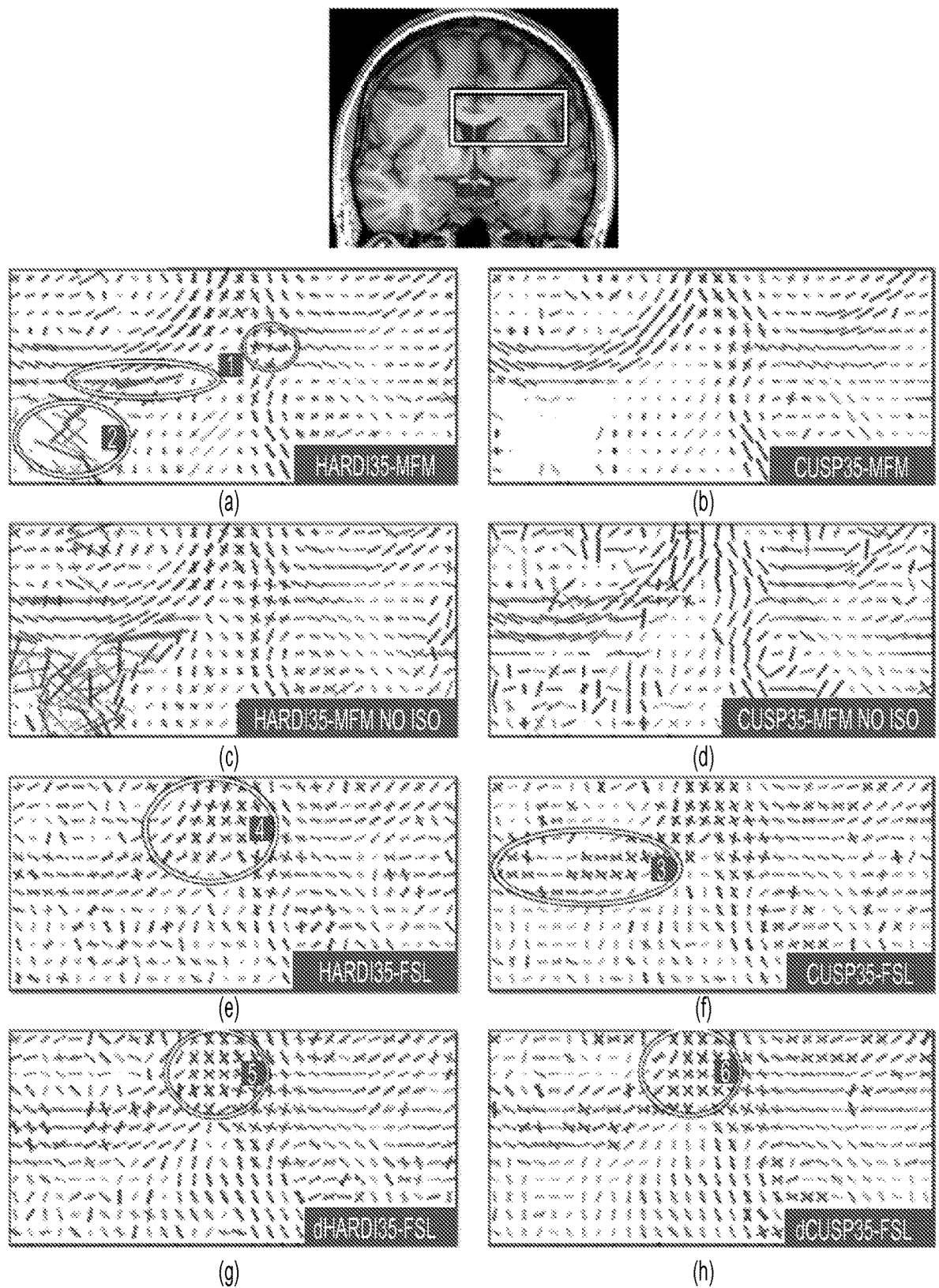
FIG. 11 illustrates an evaluation of diffusion estimates for different diffusion-weighted image acquisition schemes used in accordance with some embodiments.

FIG. 11 qualitatively compares the multi-tensor estimation performances when using a HARDI35 acquisition scheme (first column) and a CUSP35 acquisition scheme (second column) In this experiment, to fully characterize the multi-fascicle model approach described herein, no model order selection was employed but $N_f=2$ tensors at each voxel were estimated. Tensors with estimated fraction of occupancy lower than 0.05 were, however, not visualized. In the first line of FIG. 11 the results of HARDI35-MFM (FIG. 11A) and CUSP35-MFM (FIG. 11B) are compared. HARDI35-MFM led to tensors with degenerate tensor size (areas 1), and led to non-null tensors in the CSF (area 2), confounding isotropic water fraction and mixture of fascicles. In contrast, CUSP35-MFM achieves a better tensor uniformity.

FIG. 11C and FIG. 11D report the results of HARDI35-MFM and CUSP35-MFM but without the estimation of the isotropic compartment. These figures show that ignoring the isotropic compartment has substantially more impact when using CUSP35 (see FIG. 11D). FIG. 11E and FIG. 11F report the results of the ball and stick model of FSL. Use of this model results in distinct estimated sticks in the body of the corpus callosum (area 3), a region known to contain a single fascicle orientation. Additionally, sticks with orientations matching poorly the known anatomy are estimated (area 4). Thirty-five directions is maybe not enough for this MCMC Bayesian ball-and-stick model to be accurately estimated. Applying a preprocessing noise-correction filter (FIG. 11G and FIG. 11H) improves the results but creates anatomically implausible crossings (areas 5 and 6).

Figure 12:
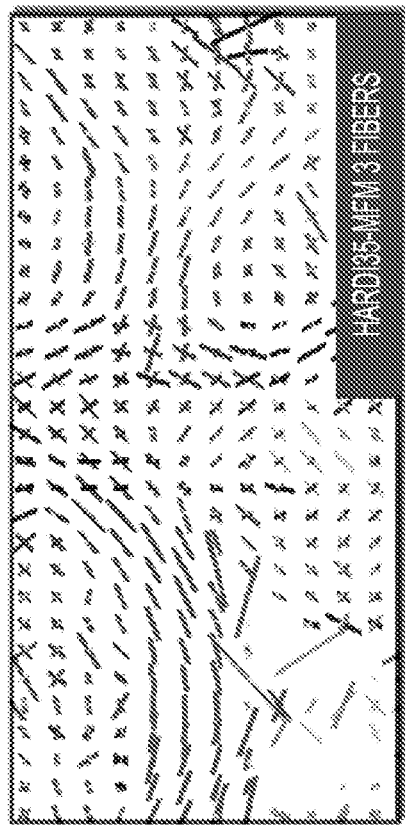
FIG. 12 illustrates an evaluation of diffusion estimates for different diffusion-weighted image acquisition schemes used in accordance with some embodiments.
Figure 12:
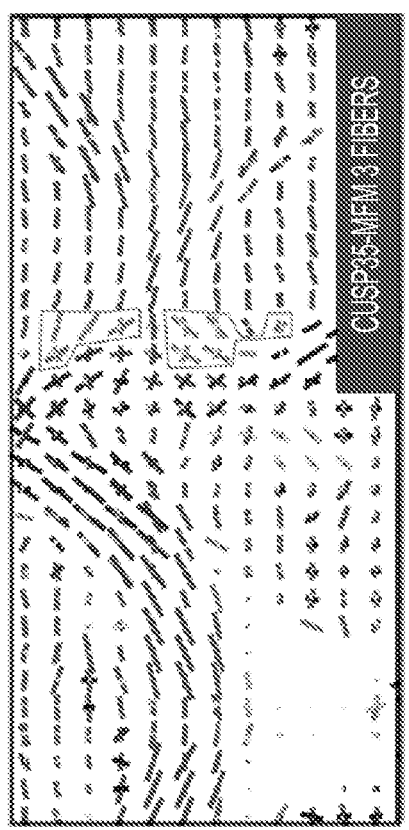

FIG. 12 reports, for the same coronal slice, the MFM estimation results with $N_f=3$ fascicles at each voxel without model order selection. Again, HARDI35-MFM leads to tensors with a degenerate size, and confounds the estimation of the isotropic water fraction and of the fascicles. In contrast, with CUSP35-MFM, the location of voxels in which three distinct fascicles are estimated with non-null fractions matches the known anatomy, whereas only 35 images were acquired. Additionally, the estimated orientation in the body of the corpus callosum matches the anatomy, whereas $N_f=3$ tensors were estimated at each voxel.

Figure 13:
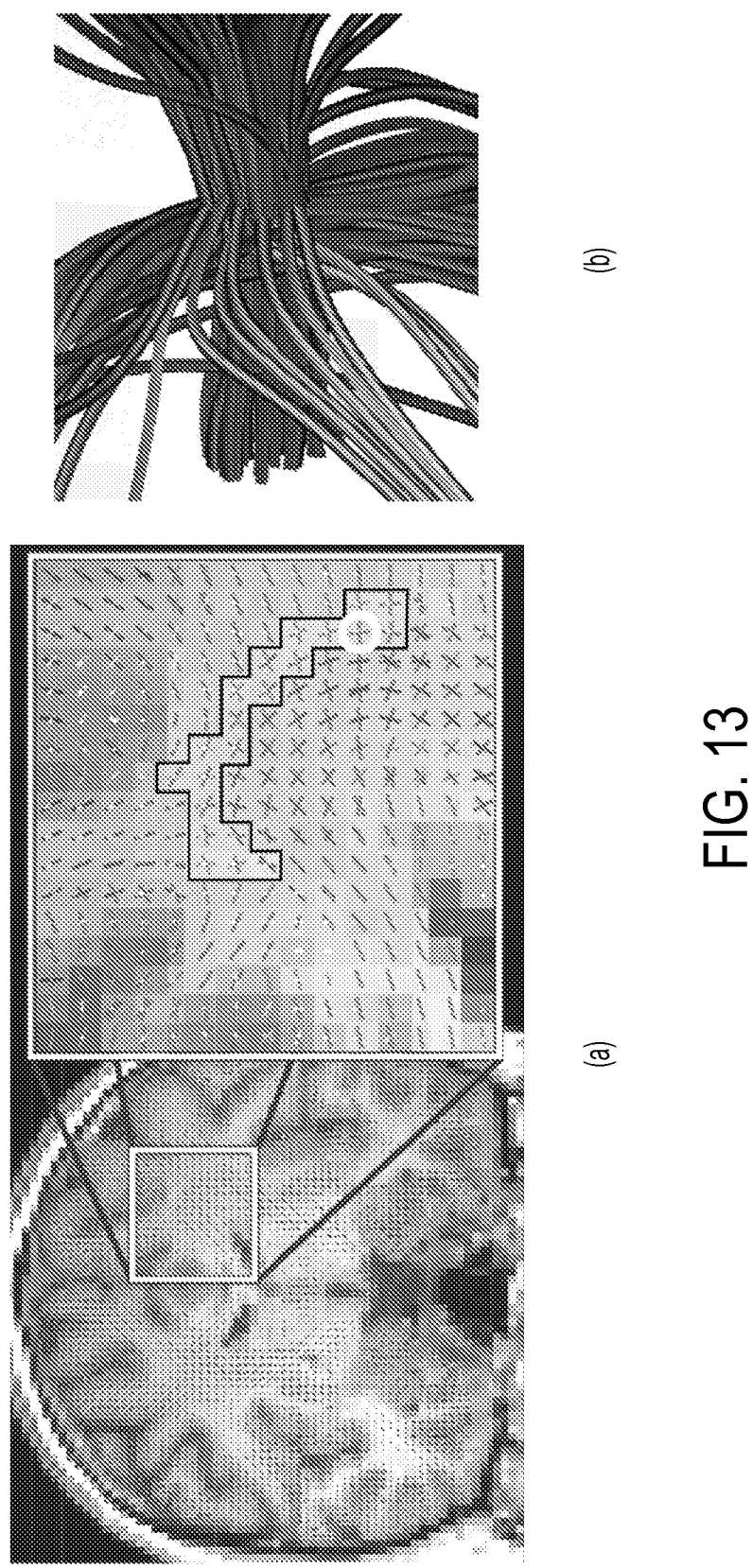
FIG. 13 shows diffusion estimates using an F-test model order selection and CUSP-65 acquisition in accordance with some embodiments.

FIG. 13 shows the CUSP-MFM estimation results when using the CUSP-65 acquisition and the F-test model order selection with a maximum of $N_f=3$ fascicles. Again, it shows estimated tensors that match the anatomy. Particularly, the outlined three tensor models correspond to a known region in the centrum semiovale where three fascicles are crossing.

Figure 14:
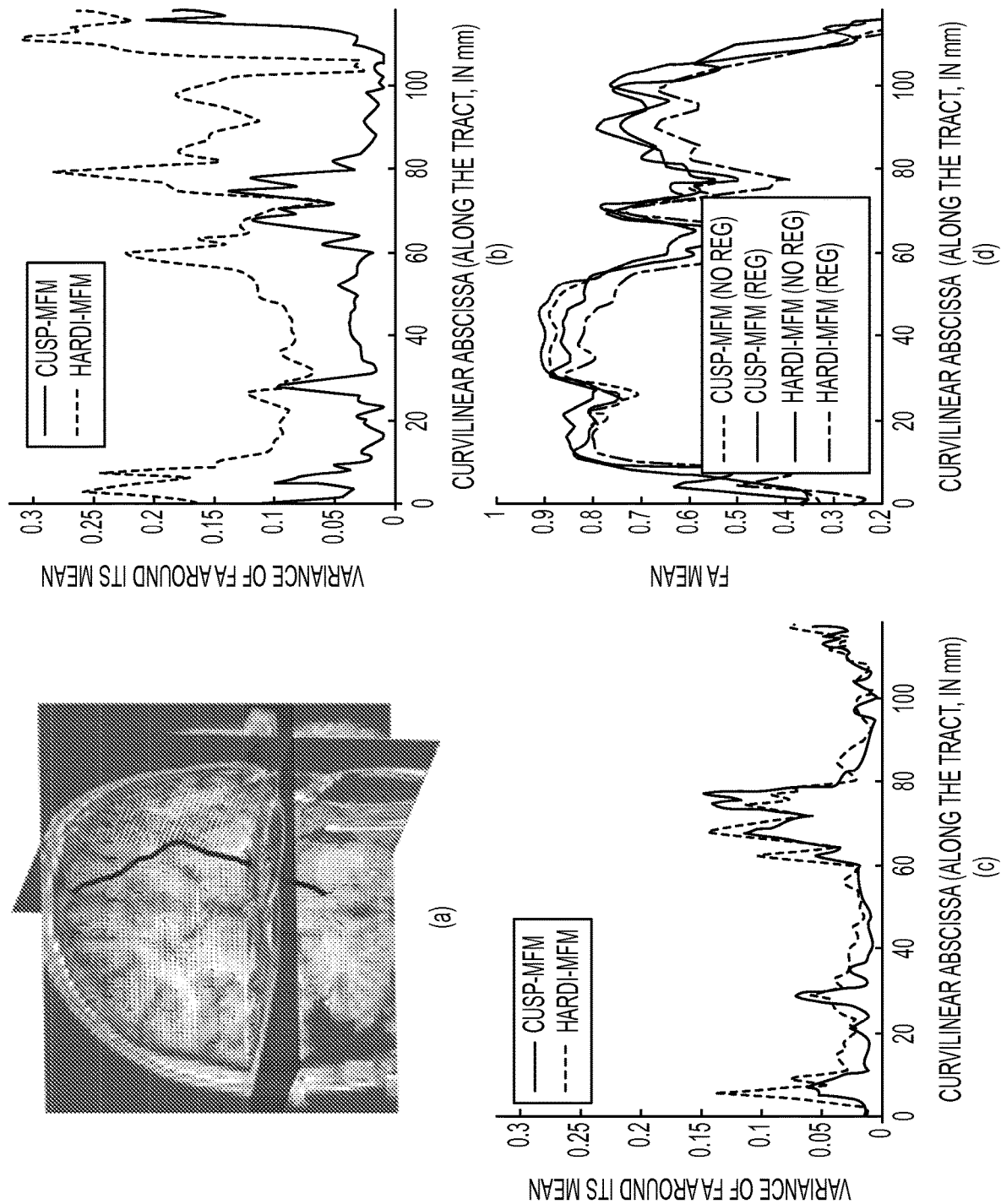
FIG. 14 illustrates that the CUSP-MFM technique used in accordance with some embodiments, enables the estimation of diffusion tensor parameters which do not vary with the partial volume effect.

FIG. 14 demonstrates how CUSP-MFM enables the estimation of the full multi-tensor, including the fractions of occupancy of each tensor. Different rotations of the diffusion-weighted images were performed to simulate various partial volume effects. A reference tract belonging to the corticospinal tract was selected (see FIG. 14A), the same rotation to each tract point was applied, and the fractional anisotropy was assessed along the tract across the rotations. FIG. 14B shows the variance of the FA when the MFM is estimated without any regularization, with CUSP35 and with HARDI35. It shows that the FA variance is much larger with HARDI35, because using an acquisition with a single non-zero b-value does not enable the full multi-tensor estimation. In contrast, the FA variance is reduced with CUSP35. FIG. 14C shows that when adding the regularization, the FA variance is reduced for both HARDI35 and CUSP35. However, as shown on FIG. 14D, adding the regularization has a significant impact on the mean of the FA with HARDI35, but not with CUSP35. With HARDI35, the regularization better constrains the optimization but leads to a wrong solution. In contrast, CUSP-MFM enables estimation of the full multi-tensor model, and consequently estimation of diffusion tensor parameters which do not vary with the partial voluming nor the regularization.

Figure 15:
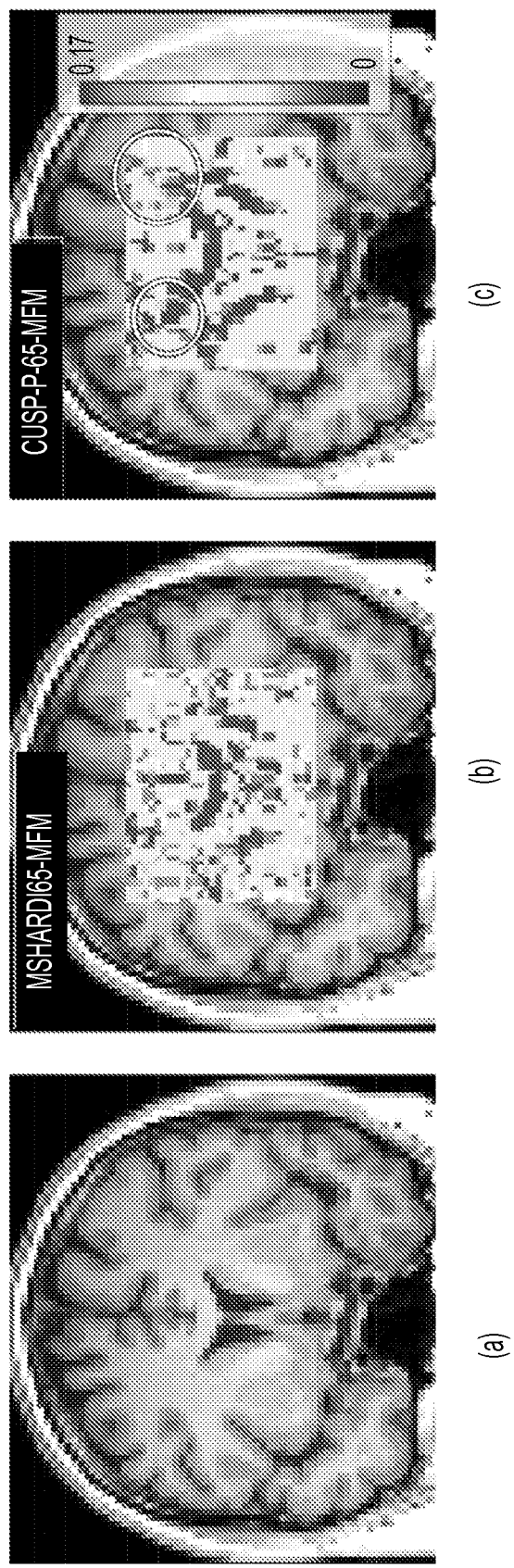
FIG. 15 shows a comparison of the CUSP acquisition technique used in accordance with some embodiments and a multi-shell HARDI acquisition technique.

FIG. 15 reports the results of the residual bootstrap analysis, illustrating the benefits of employing CUSP instead of a multi-shell HARDI. From the initially fitted multi-fascicle model, five hundred new virtual acquisitions were generated. For each virtual acquisition, the MFM was estimated at each voxel and the maximum FA of the estimated fascicles was computed. The maximum FA was used as a proxy to identify the same fascicle across multiple iterations of the bootstrap analysis. FIG. 15A and FIG. 15B show the variance of the FA of the fascicle with the largest FA over the five hundred bootstrap iterations, respectively for MSHARDI-65-MFM and CUSP-65-MFM. It shows the uncertainty when estimating the fascicle of higher FA at each voxel. The uncertainty in FA is significantly lower with CUSP compared to the multi-shell HARDI, because MSHARDI-65 requires a larger TE to achieve a nominal b-value of 3000 s/mm2 which leads to an acquisition with lower SNR.

Several conventional techniques have been investigated to overcome the limitations of DTI and to represent multiple white matter fascicles from diffusion-weighted imaging. Approaches such as DSI, QBI, EQBI, DOT, SD or GDTI focus on estimating the global shape of the diffusion profile resulting from multiple fascicles present in each voxel. The major drawback is they do not consider each fascicle independently. Consequently, they do not enable characterization of each fascicle, and do not enable comparison of the fascicle characteristics between individuals. The assessment of parameters such as the generalized fractional anisotropy (GFA) or the generalized mean diffusivity (GMD) has also been proposed. However, these measures do not represent a fascicle property but a dispersion property of the diffusion signal inside each voxel. For example, a synthetic uniform fascicle can be simulated by considering an identical tensor at each voxel. Such a uniform fascicle crossed by another synthetic fascicle has a GFA that varies in the crossing region because the dispersion of the diffusion signal is different in the crossing region. Therefore, the GFA which represents a voxel property provides misleading data. A uniform fascicle should have constant diffusion parameters along its path. This limitation reduces the scope of DSI, QBI, EQBI, DOT, or GDTI to connectivity analysis. In addition, these approaches generally require a relatively high number of DWI acquisitions, limiting their use in clinical practice. Prior efforts have demonstrated through Monte Carlo simulations of a model of diffusion in cylinders of a certain size range with certain permeability characteristics, that the signal measured by a single shell HARDI acquired at $b=3000$ s/mm$^2$ (with timing parameters achievable on a clinical MRI scanner) arises primarily from restricted water. Under these assumptions, the amount of signal can be related to the underlying density of white matter fascicles, thus enabling the formation of a measure of the 'apparent fiber density'. In addition, the orientation of white matter fascicles can be determined from the local signal maxima.

In contrast, the multi-fascicle model (MFM) described herein enables the determination of the orientation of the white matter fascicles, measures of their local diffusion properties and the characterization of an unrestricted water component that is important in assessing edema and inflammation. Multi-fascicle approaches generally require the determination of the number of white matter fascicles at each voxel. This and only this enables characterization of each fascicle in addition to the orientation information, which is of central interest to study the white matter development or degeneration in research and clinical practice. Recently, it has been proposed to estimate a general ODF at each voxel and then fit tensors on the ODF to extract geometric features of the peaks. However, this requires the estimation of the ODF, which is sensitive to noise and requires a high number of DW images. In contrast, direct estimation of a MFM from the DW images enables representation of multiple fascicles and involves a small number of parameters, requiring potentially a small number of acquisitions. MFMs allow the computation of diffusion parameters such as the FA for each fascicle, which facilitates straightforward characterization of multiple fascicles.

Multi-tensor models have however frequently been reported to be numerically challenging and unstable. Among others, Kreher et al. have observed that with a model including one entirely isotropic diffusion tensor and multiple entirely anisotropic tensors, the mean diffusion and the relative ratio of components could not be separated with DW images measured at a single high b-value. As described herein, it has been shown that the reason lies in a collinearity in the parameters when a single non-zero b-value acquisition is employed, leading to an infinite number of solutions. With only one non-zero b-value, the tensor size indicated by the magnitude of its eigenvalues and the estimated volume fractions are collinear. Consequently, fitting them together may make a fascicle with a uniform $D_j$ across its entire length grow and shrink as it passes through voxels and experiences different partial volume effects. Algebraically one constraint in the modeling could resolve this ambiguity: imposing a symmetry between the tensors' eigenvalues such as $\lambda_{1,1}=\lambda_{2,1}$ Such a constraint is however not suited to accurately characterize each fascicle independently. The fractions of occupancy may also be merged together. This, however, does not adequately represent the signal arising from each fascicle in presence of partial volume effect, and does not allow the computation of a full diffusion tensor associated with each white matter fascicle. Only the use of multiple non-zero b-values is a satisfying solution to disambiguate the estimation of the tensors and the fractions, and to enable characterization of each individual fascicle and of the unrestricted water component.

The techniques described herein describe a novel multi-fascicle estimation framework, CUSP-MFM, which is the combination of a novel multi-tensor estimation algorithm and an optimal acquisition scheme which satisfies the need of multiple non-zero b-values. The characteristics of the multi-tensor estimation technique were driven by the objective to make it possible to represent multiple fascicles in clinical DWI with a relatively short acquisition time, compatible with pediatric and adult imaging. The Maximum A Posteriori formulation that was employed enabled performance of accurate and reliable multi-fascicle model estimation. The MFM includes the estimation of an isotropic tensor which represents the free population of water molecules that is not affected by fiber structure barriers. In the experiments reported herein, a dramatic impact of adding this parameter was not observed when using a single-shell HARDI (FIG. 11A and FIG. 11C). In this case, there is no unique solution to the estimation due to the collinearity of the parameters, and the part of the DW signal coming from the free water population is incorporated in the tensor magnitude and in the fractions. In contrast, with multiple non-zero b-values (e.g., CUSP), the tensor magnitude and the fractions are not collinear. It was demonstrated that the attempt to fit a model without the isotropic water compartment, i.e., a model that poorly represents the signal, perturbs the whole tensor estimation (FIG. 11D). Therefore, to ensure reliable estimates, both multiple non-zero b-values and a model that accounts for the unrestricted water diffusion are recommended.

When using an optimized acquisition scheme and when estimating the diffusion of unrestricted water, the fascicle orientation from the hindered diffusion can be accurately estimated. The results of the experiments described herein relied on the assumption that, for each fascicle, the DW signal mono-exponentially decays with increasing b-value. Based on non-monoexponential decays measurements in voxels, it has been suggested that a non-monoexponential model may be more appropriate, even for relatively low b-values. However, these approaches have ignored the fascicle orientation heterogeneity ($N_f=1$) and the CSF contamination when considering a model with non-monoexponential decay. In this case, the source of the non-monoexponential decay remains unclear. As illustrated in FIG. 2, mixing of monoexponential decays as modeled in the approach described herein does lead to a non-monoexponential behavior in voxels. When the gradient strength is limited and when the DW signal is properly modeled by taking into account both the fascicle orientation heterogeneity ($N_f>1$) and the CSF contamination, a monoexponential decay for the signal arising from each fascicle can be safely assumed. In contrast, if the diffusion signal of a single fascicle exhibits a non-monoexponential decay, then the multi-fascicle model described herein cannot fully represent it and a generalization of this model may be necessary. Other per-fascicle models could be introduced in our framework and may be investigated in future work.

The present disclosure formulates a multi-tensor estimation approach in the log-Euclidean framework which is an elegant way to guarantee that each tensor matrix is symmetric positive definite during the fitting. A Cholesky parameterization of the diffusion tensor or Bayesian approaches with priors on the eigenvalues to ensure valid tensors have also been considered. With the log-Euclidean framework, all computations are performed within the appropriate manifold, ensuring valid tensors at each step. The log-Euclidean framework has not been typically employed for multi-fascicle models. Not only does it ensure non-degenerate tensors, it also provides a metric to compare and regularize tensors. All of the information carried by tensors is taken into account with the log-Euclidean metric, and not only features extracted from the tensors Importantly, tensor determinants in this framework are monotonically interpolated. It prevents the regularized tensors from experiencing the swelling effect which has been observed in both the Euclidean and Cholesky frameworks. The swelling effect makes the estimated tensors larger than they should be. It particularly affects tensors at tissue borders such as the cerebrospinal fluid/white matter interface, where neighboring tensors are very dissimilar. Based on Monte Carlo experiments, it has been suggested that an affine-invariant metric such as the log-Euclidean metric might lead to a larger bias in the case of extreme ADC values (either low or high). However, for the major brain tissues, this bias is not observed.

A log-Euclidean regularization scheme, as discussed herein is not the direct extension of the one-tensor regularization. Rather, a particular approximation of the spatial gradient for multi-tensor fields is provided (equation (5)) that relates neighboring tensors which are part of the same fascicle. Consequently, only tensors which are part of the same fascicle are regularized together. Introducing this regularization strategy is possible because each fascicle is considered independently. Such a regularization may be difficult to integrate in DSI, QBI, GDTI, or SD because these approaches consider the general shape of the diffusion profile and not individual fascicles.

Embodiments of the present disclosure describe acquisition techniques designed to enable accurate assessment of multiple white matter fascicles. The CUSP (CUbe and SPhere) imaging technique combines a single-shell HARDI with gradients in its enclosing cube (i.e., the cube of constant TE). The single-shell HARDI provides a full spherical sampling with an optimal SNR and optimal TE for the chosen nominal b-value. Any gradient in the enclosing cube of the single-shell HARDI can be acquired without modifying the TE by choosing the appropriate gradient strength. The techniques described herein enable acquisition of b-values up to three times the nominal b-value while achieving the same low TE as a single-shell HARDI. Consequently, and in contrast to multi-shell HARDI, the acquisition techniques described herein do not increase the imaging time, do not increase the eddy current distortion and maintain the DWI signal-to-noise ratio by maintaining exp(−TE/T2).

Three variations on the generalized CUSP acquisition technique are described herein (FIG. 4) for selecting gradients within the cube of constant TE. It should be appreciated however, that any other suitable technique may be used to select gradients for the CUSP acquisition technique, and the variations described herein are merely provided for illustrative purposes.

Figure 5:
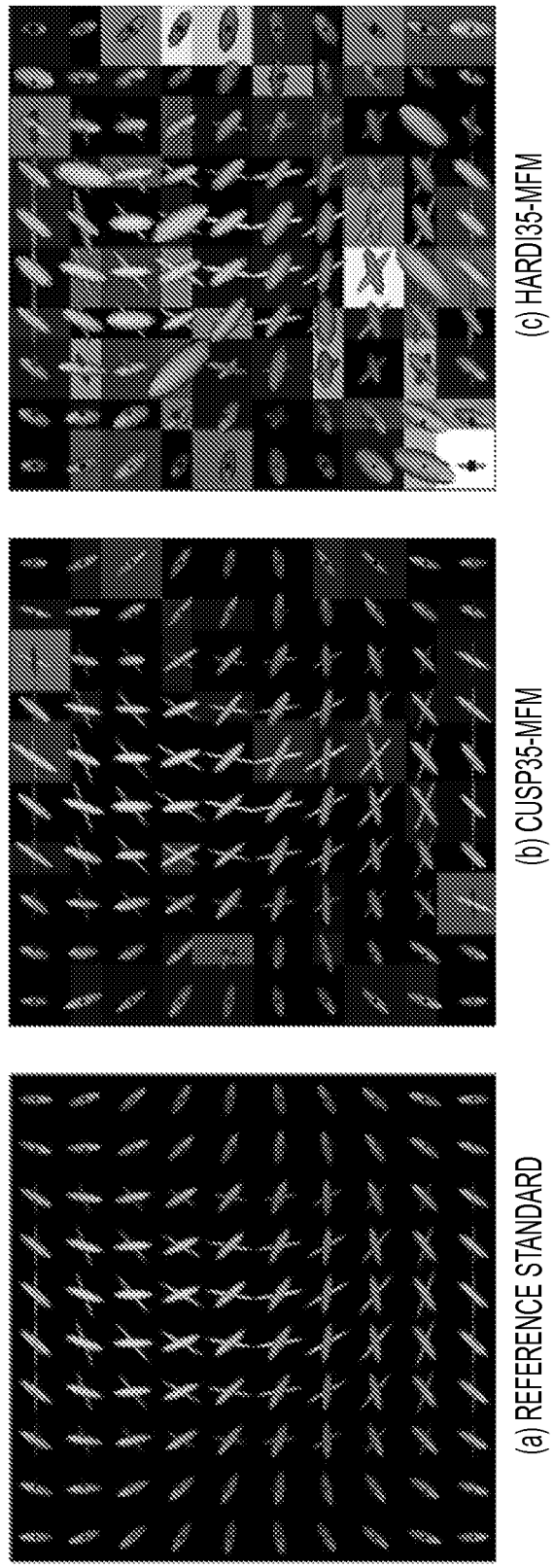
FIG. 5 shows a qualitative evaluation of the CUSP-MFM technique used in accordance with some embodiments.

The experiments described herein show evidence that the estimation of both the tensors and the fractions of occupancy are improved when using CUSP instead of a single shell acquisition (FIG. 5, 6, 9). Additionally, a substantial improvement of the angular resolution was observed when using CUSP instead of a single shell HARDI (FIG. 7). From an algebraic point of view, only the tensor magnitude and the fractions are collinear with a single non-zero b-value. Introducing several non-zero b-values should not impact the tensor eigenvectors in a noise free model system. However, we observed that introducing higher b-values helps in differentiating the different compartments. Consequently, CUSP provides at least three benefits: it solves the collinearity inherent to the multi-fascicle modeling with a single-shell HARDI, it enables imaging at higher b-values, which facilitates the estimation of the orientation of each fascicle, and when compared to a conventional single-shell HARDI acquisition, it does not increase the acquisition time, does not increase the eddy current distortion, and does not alter the signal-to-noise ratio.

Figure 9:
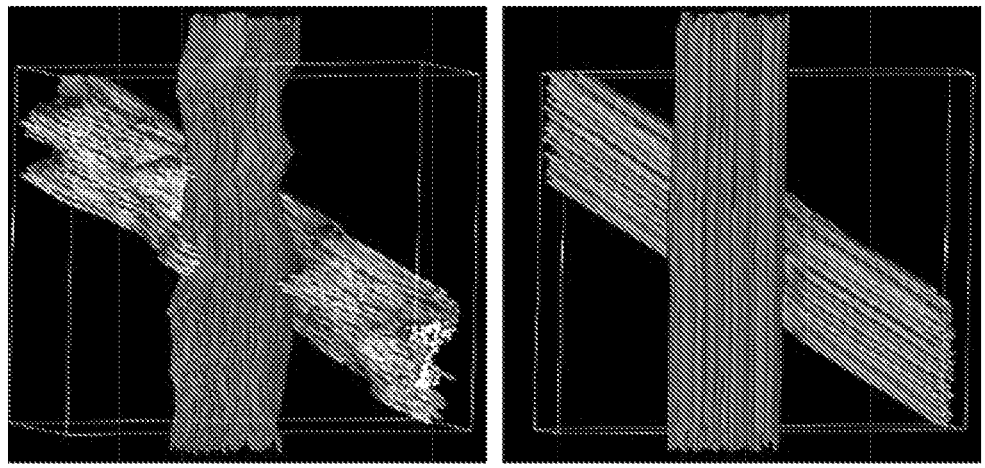
FIG. 9 shows an estimation of two synthetic crossing fascicles with the CUSP-MFM technique used in accordance with some embodiments.
Figure 9:
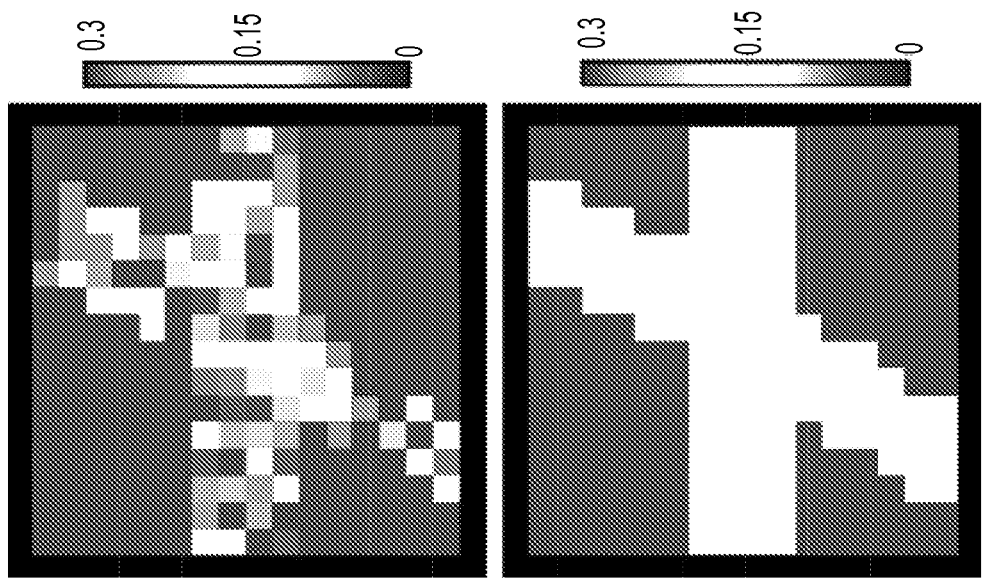
Figure 9:
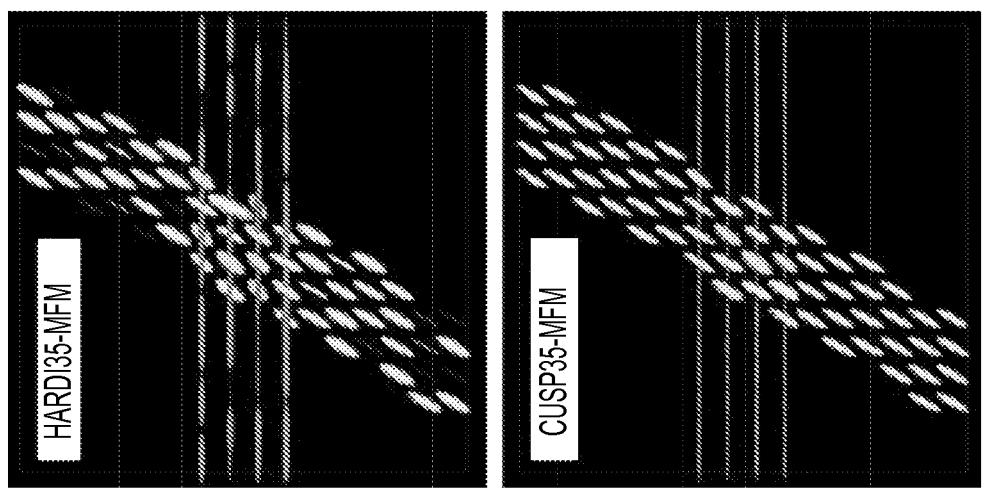

The performance of CUSP-MFM was assessed via various experiments on both synthetic and in vivo data. Short acquisitions suitable for routine clinical use, especially for pediatric MM were the focus of these experiments. It was found that the angular resolution is substantially superior to the state-of-the-art ball-and-stick model implemented in FSL (FIG. 7), while CUSP-MFM estimates the full tensor. This might be explained by the fact that the stick is an over-simplification which does not fully capture the true signal arising from a fascicle. Incorrect estimation of the tensor eigenvalues perturbs the estimation of the orientation because the optimization attempts at fully explaining the DW signal with an unrealistic model, leading to less accurate estimates. This also leads to the detection of multiple sticks in the body of the corpus callosum, which is a known single fascicle region (FIG. 11). In contrast, CUSP-MFM incorporates a more complex model for each fascicle and enables the assessment of individual fascicles characteristics in addition to the brain connectivity, by computing diffusion tensor parameter for each fascicle. The estimated diffusion parameters of two uniform synthetic crossing fascicles were shown to be almost uniform with CUSP-MFM (FIG. 9 and FIG. 10). It was verified on real acquisitions by simulating variations of the partial volume fractions for each tensor, by rotation of the diffusion-weighted images with various angles. With CUSP-MFM, it was shown that the fractional anisotropy computed along a tract did not vary with the partial voluming effect nor the regularization, which was not the case when using a single-shell HARDI acquisition (FIG. 14). CUSP-MFM enables the full estimation of the multi-fascicle model, which enables characterization of the fascicles.

FIG. 6 showed that for small angles and in the absence of model order selection, the reconstruction error for the fractions of occupancy (fAAD) is significantly increased. Indeed, in the case where $D_1 = D_2$: $f_1 e^{-b_k g_k^T D_1 g_k} + f_2 e^{-b_k g_k^T D_1 g_k} = (f_1 + f_2) e^{-b_k g_k^T D_1 g_k} + 0$. It is not possible to estimate the fractions of occupancy $f_1$ and $f_2$ because of a collinearity in the parameters. The DW signal can be explained either with two compartments with non-null fractions $f_1$ and $f_2$ or with a single compartment with fraction $(f_1 + f_2)$. This case $(D_1 \approx D_2)$, however, can be easily detected and handled with model order selection.

The qualitative evaluation on real data (FIGS. 11, 12, 13) showed that the estimated tensors orientation matches the expected underlying anatomy. The estimation without model order selection (FIGS. 11, 12) showed that CUSP-MFM recovers the fascicle orientations better than the ball-and-stick model in regions of a single fascicle, either with $N_f=2$ or $N_f=3$ Importantly, the estimation of $N_f=3$ fascicles with only 35 DW-images was consistent with the anatomy (FIG. 12). Additionally, in contrast to HARDI-MFM, CUSP-MFM enables correct estimation of the isotropic water fraction in the CSF (FIGS. 11, 12).

Additionally, it was demonstrated that the estimation uncertainty is higher when using a multi-shell HARDI instead of CUSP (FIG. 15). This is due to the larger minimum achievable TE when imaging the full multi-shell HARDI, leading to an acquisition with exponentially decreased SNR (e.g., see equation (1) and FIG. 1).

Future work may focus on assessing different gradient schemes for the CUSP acquisition. Particularly, the optimal ordering of the gradient directions may be investigated. CUSP-MFM performance may be compared to Q-Ball Imaging and Spherical Deconvolution approaches for the assessment of connectivity.

Robust estimation may also explored. It enables to reduce the influence of large residuals, making the estimation less sensitive to outliers than when using the least square criteria. It may provide a better robustness to patient motion and will be of particular interest for pediatric imaging.

The techniques described herein demonstrate and experimentally verify that multiple non-zero b-values are required to fully estimate multi-tensor models. As a illustrative solution, a CUSP-MFM technique, which combines a CUbe and SPhere (CUSP) acquisition technique with an algorithm for the estimation of the parameters of a Multi-Fascicle Model (MFM), is described. The CUSP acquisition technique provides multiple high b-values with an optimal achievable TE. It does not increase the imaging time nor the eddy current distortion compared to a single-shell HARDI. Additionally, it provides an optimal signal-to-noise ratio, leading to estimates with higher certainty. The multi-fascicle fitting algorithm MFM described herein is formulated as a Maximum A Posteriori estimation problem. It integrates an isotropic compartment, constrained estimation and an original regularization scheme in which only the tensors that are part of the same tract are regularized together. It ensures non-degenerate tensors and robust-to-noise estimates. An evaluation of the model shows that CUSP-MFM enables the representation of multiple white matter fascicles from a short duration acquisition. It enables characterization of each fascicle, in addition to the brain connectivity, which is of great interest for clinical applications. CUSP-MFM may enable new investigations of the white matter development and degeneration in research and in clinical practice.

Exemplary CUSP Gradient Encoding Scheme

Below is an exemplary CUSP-P-65 gradient encoding scheme in the Siemens format. On a Siemens scanner, this requires to set the imaged b-value to b=3000 s/mm² which corresponds to the b-value of the gradient of higher norm in the table. With this choice, the resulting minimum achievable TE correctly matches the minimum achievable TE of a single-shell HARDI at b=1000 s/mm²

```
[directions-65]
CoordinateSystem = xyz
Normalisation = none
Vector[0] = (0, 0, 0)
Vector[1] = (0, 0, 0)
Vector[2] = (0, 0, 0)
Vector[3] = (0, 0, 0)
Vector[4] = (0, 0, 0)
Vector[5] = (1.00000. 0.00000, 0.00000)
Vector[6] = (0.16600, 0.98600, 0.00000)
Vector[7] = (0.11000, −0.66400, −0.74000)
Vector[8] = (0.90100, −0.41900, −0.11000)
Vector[9] = (0.16900, 0.60100, −0.78100)
Vector[10] = (0.81500, 0.38600, −0.43300)
Vector[11] = (−0.65600, −0.36600, −0.66000)
Vector[12] = (−0.58200, −0.80000, −0.14300)
Vector[13] = (−0.90000, −0.25900, −0.35000)
Vector[14] = (−0.69300, 0.69800, −0.17800)
Vector[15] = (0.35700, −0.92400, −0.14000)
Vector[16] = (0.54300, −0.48800, −0.68300)
Vector[17] = (0.52500, 0.39600, −0.75300)
Vector[18] = (0.63900, −0.68900, −0.34100)
Vector[19] = (−0.33000, −0.01300, −0.94400)
Vector[20] = (0.52400, 0.78300, −0.33500)
Vector[21] = (0.60900, −0.06500, −0.79100)
Vector[22] = (0.22000, −0.23300, −0.94700)
Vector[23] = (−0.00400, −0.91000, −0.41500)
Vector[24] = (−0.51100, 0.62700, −0.58900)
Vector[25] = (−0.41400, −0.73700, −0.53500)
Vector[26] = (−0.67900, 0.13900, −0.72100)
Vector[27] = (−0.88400, 0.29600, −0.36200)
Vector[28] = (−0.26200, −0.43200, −0.86300)
Vector[29] = (0.08800, 0.18500, −0.97900)
Vector[30] = (−0.29400, 0.90700, −0.30200)
Vector[31] = (0.88700, −0.08900, −0.45300)
Vector[32] = (−0.25700, 0.44300, −0.85900)
Vector[33] = (0.08600, 0.86700, −0.49100)
Vector[34] = (0.86300, 0.50400, −0.02500)
Vector[35] = (−1.00000, −1.00000, −1.00000)
Vector[36] = (1.00000, −1.00000, −1.00000)
Vector[37] = (−1.00000, 1.00000, −1.00000)
Vector[38] = (1.00000, 1.00000, −1.00000)
Vector[39] = (1.00000, 1.00000, 0.00000)
Vector[40] = (−0.00000, −1.00000, −1.00000)
Vector[41] = (−1.00000, −0.00000, −1.00000)
Vector[42] = (−1.00000, 1.00000, 0.00000)
Vector[43] = (−0.00000, 1.00000, −1.00000)
Vector[44] = (1.00000, −0.00000, −1.00000)
Vector[45] = (1.00000, −0.11968, −0.22826)
Vector[46] = (0.45391, 1.00000, −0.74490)
Vector[47] = (0.30929, −0.52908, −1.00000)
Vector[48] = (1.00000, 0.32570, −0.82547)
Vector[49] = (−0.53649, −0.28378, −1.00000)
Vector[50] = (1.00000, 0.28277, −0.16662)
Vector[51] = (0.37769, 0.13072, −1.00000)
Vector[52] = (−0.18512, 0.21731, −1.00000)
Vector[53] = (−0.32054, −1.00000, −0.32795)
Vector[54] = (0.37433, 1.00000, −0.18999)
Vector[55] = (−1.00000, 0.49160, −0.79472)
Vector[56] = (−0.09712, 1.00000, −0.03398)
Vector[57] = (−1.00000, −0.00905, −0.41514)
Vector[58] = (0.36282, −1.00000, −0.54229)
Vector[59] = (−0.52123, 1.00000, −0.11772)
Vector[60] = (−0.31196, 1.00000, −0.73018)
Vector[61] = (−1.00000, −0.69636, −0.40808)
Vector[62] = (−1.00000, 0.32257, −0.12697)
Vector[63] = (1.00000, −0.48206, −0.55084)
Vector[64] = (−0.06116, −0.17609, −1.00000)
```

Figure 16:
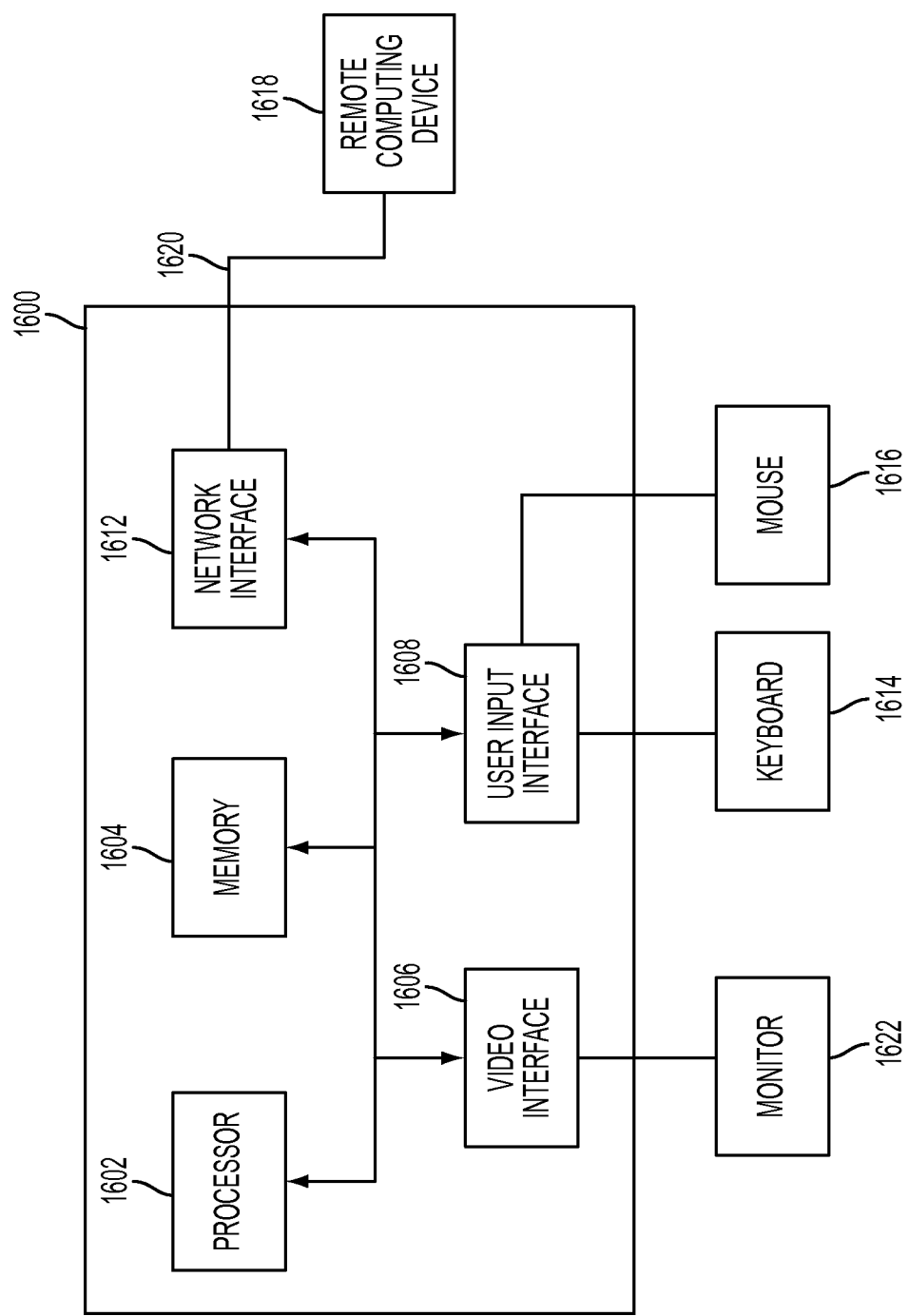
FIG. 16 is an exemplary computer system on which some embodiments may be implemented.

FIG. 16 shows a schematic block diagram of an illustrative computer 1600 on which features may be implemented. Only illustrative portions of the computer 1600 are identified for purposes of clarity and not to limit aspects of the invention in any way. For example, the computer 1600 may include one or more additional volatile or non-volatile memories, one or more additional processors, any other user input devices, and any suitable software or other instructions that may be executed by the computer 1600 so as to perform the function described herein. For example, the EEG data may be sent directly from a wireless EEG headset to a smartphone or cell phone and may be relayed directly to the remote computing device 1618.

In the illustrative embodiment, the computer 1600 includes a system bus 1610, to allow communication between a central processing unit 1602, a memory 1604, a video interface 1606, a user input interface 1608, and a network interface 1612. The network interface 1612 may be connected via network connection 1620 to at least one remote computing device 1618. Peripherals such as a monitor 1622, a keyboard 1614, and a mouse 1616, in addition to other user input/output devices may also be included in the computer system, as embodiments are not limited in this respect.

Figure 17:
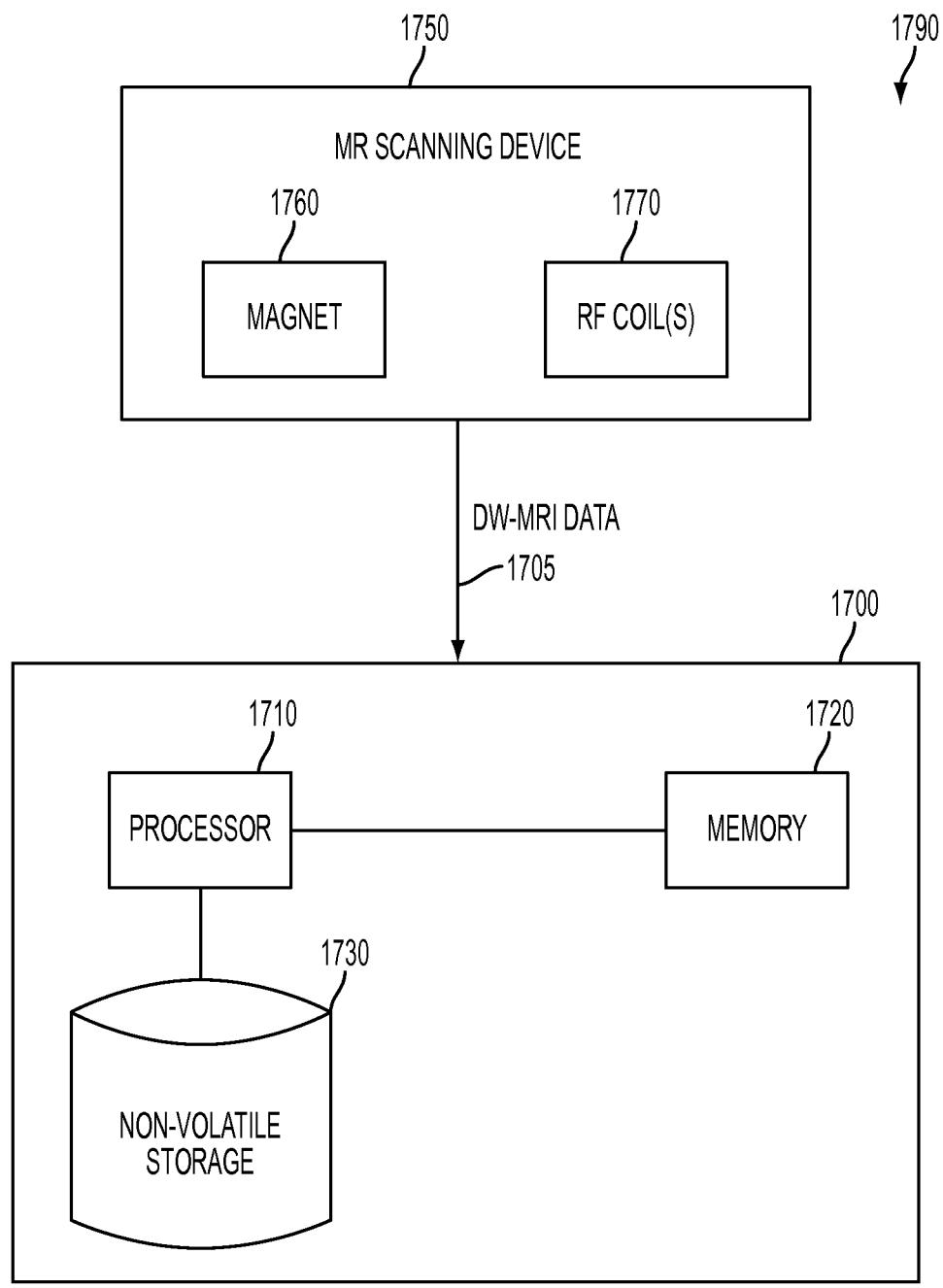
FIG. 17 illustrates a MR scanning device suitable for obtaining DW-MRI data in accordance with some embodiments.

FIG. 17 illustrates a block diagram of one embodiment of a system 1790 suitable for practicing various techniques described herein. System 1790 comprises a magnetic resonance (MR) scanning device 1750 and computer system 1700. MR scanning device 1750 may be any device capable of obtaining MR data and, in particular, capable of acquiring DW-MRI data. For example, MR scanning device 1750 may include a magnet 1760 capable of producing a magnetic field of desired strength, and may produce a uniform or gradient magnetic field. Magnet 1760 may be of any shape, size and strength and may include multiple magnets of any size, shape and strength.

MR scanning device 1750 also comprises one or more RF coils 1770 arranged proximate the magnet and adapted to provide RF pulse sequences to an object being scanned and/or to detect NMR signals (e.g., DW-MRI signals) emitted therefrom. RF coils 1770 may comprise one or multiple coils arranged in any configuration to perform single coil acquisition or multiple coil acquisition (i.e., parallel MR). RF coils 1770 may include independent RF coils for providing RF pulse sequences (excitation coils) and detecting NMR signals (receive coils), or one or more RF coils may be arranged as both an excitation and receive coils. Any configuration of magnet 1760 and RF coil(s) 1770 may be suitable, as the techniques described herein are not limited for use on data obtained from any particular MR scanning device.

Computer system 1700 may be used to implement one or more techniques described herein. Computer system 400 may include one or more processors 1710 and one or more non-transitory computer-readable storage media (e.g., memory 1720 and one or more non-volatile storage media 1730). The processor 1710 may control writing data to and reading data from the memory 1720 and the non-volatile storage device 1730 in any suitable manner Processor 1710, for example, may be a processor on any device, for example, a personal computer, a workstation, one or more servers, or may be a processor on-board or otherwise integrated with MR scanning device 1750, etc.

To perform functionality and/or techniques described herein, the processor(s) 1710 may execute one or more instructions stored in one or more computer-readable storage media (e.g., the memory 1720, storage media, etc.), which may serve as non-transitory computer-readable storage media storing instructions for execution by processor(s) 1710. Computer system 1700 may also include any other processor, controller, or control unit needed to route data, perform computations, perform I/O functionality, etc. For example, computer system 1700 may include any number and type of input functionality to receive data and/or may include any number and type of output functionality to provide data, and may include control apparatus to perform I/O functionality.

Computer system 1700 may be integrated into MR scanning device 1750 or may be a separate stand-alone computer system, either proximate to or remote from MR scanning device 450. For example, computer system 1700 may be connected to MR scanning device 1750 over a network, connected to multiple scanning devices or may not be connected to any scanning device at all. When computer system 1700 is connected to or integrated with MR scanning device 1750, computer system 1700 may be programmed to control the RF coil(s) according to a desired RF sequence or protocol, or MR scanning device 1750 may have a separate controller to perform excitation and acquisition.

When computer system 1700 is separate from MR scanning device 1750, computer system 1700 may operate on MR data (e.g., DW-MRI data) previously stored on computer system 1700, may obtain DW-MRI data from some other location, e.g., another computer system, over a network, or may obtain the DW-MRI data via transportable storage medium, etc. It should be appreciated that any computing environment may be used, as the techniques described herein are not limited for use with a computer system of any particular type or implementation.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Through, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, embodiments may be embodied as a computer readable medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other non-transitory, tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above. As used herein, the term "non-transitory computer-readable storage medium" encompasses only a computer-readable medium that can be considered to be a manufacture (i.e., article of manufacture) or a machine.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect of this embodiment, one or more computer programs that when executed perform methods of embodiments need not reside on a single computer or processor, but may be distributed in a modular fashion amongst a number of different computers or processors to implement various embodiments.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationships between data elements.

Various aspects of embodiments may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, embodiments may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting.

What is claimed is:

1. A method for acquiring diffusion-weighted images, the method comprising:
    selecting a first set of diffusion gradient vectors, each of diffusion gradient vectors in the first set having a constant gradient strength and corresponding to a first non-zero b-value, wherein the directions of the diffusion gradient vectors in the first set are distributed on a surface of a first sphere having a first radius;
    defining a cube of constant echo image time (TE) that encloses the first sphere, wherein the cube of constant TE comprises faces and edges, and a volume inside the cube of constant TE defines a volume within which any diffusion gradient vector located therein can be applied without increasing TE; and
    selecting a second set of diffusion gradient vectors, each of the diffusion gradient vectors in the second set being located within the cube of constant TE, wherein at least one of the diffusion gradient vectors in the second set corresponds to a second non-zero b-value different from the first non-zero b-value,
    wherein at least one diffusion gradient vector in the second set extends to a face of the cube of constant TE without also extending to an edge of the cube of constant TE, and/or at least one diffusion gradient vector in the second set extends to a point within the cube of constant TE without extending to a face or an edge of the cube of constant TE; and
    acquiring the diffusion-weighted images using a gradient encoding scheme including the gradients corresponding to each of the diffusion gradient vectors in the first and second sets.

2. The method of claim 1, wherein each of the diffusion gradient vectors in the second set extends to one of the faces of the cube of constant TE.

3. The method of claim 1, wherein each of the diffusion gradient vectors in the second set extends to a point within the cube of constant TE without extending to a face or an edge of the cube of constant TE.

4. The method of claim 1, wherein the diffusion gradient vectors in the first set of diffusion gradient vectors are uniformly distributed on the surface of the first sphere.

5. The method of claim 1, wherein selecting the second set of diffusion gradient vectors comprises:
    defining a second sphere having a second radius larger than the first radius;
    specifying a plurality of diffusion gradient vectors having directions distributed on a surface of the second sphere;
    projecting each of the diffusion gradient vectors having directions distributed on the surface of the second sphere to a face or an edge of the cube of constant TE; and
    including the projected diffusion gradient vectors in the second set.

6. The method of claim 5, wherein selecting the second set of diffusion gradient values comprises: defining a third sphere having a third radius smaller than the first radius; and
    including in the second set, a plurality of diffusion gradient vectors having directions distributed on a surface of the third sphere.

7. The method of claim 6, wherein the first radius, the second radius, and the third radius are uniformly spaced.

8. The method of claim 6, wherein the first radius, the second radius, and the third radius are exponentially spaced.

9. The method of claim 5, wherein the second non-zero b-value is determined by multiplying the first non-zero b-value by a first value, and wherein defining the second sphere comprises defining the second sphere based, at least in part, on the second non-zero b-value.

10. The method of claim 1, wherein the first non-zero b-value is in the range 800 s/mm$^2$ to 1200 s/mm$^2$.

11. The method of claim 1, wherein the second non-zero b-value is in the range 2000 s/mm$^2$ to 4000 s/mm$^2$.

12. The method of claim 1, wherein at least one first diffusion gradient vector in the second set extends to a face of the cube of constant TE without also extending to an edge of the cube of constant TE and at least one second diffusion gradient vector in the second set extends to a point within the cube of constant TE without extending to a face or an edge of the cube of constant TE.

13. A magnetic resonance imaging (MRI) apparatus, comprising:
    a main magnetic field coil;
    a plurality of gradient magnetic field coils; and
    at least one computer processor programmed with a plurality of instructions that, when executed by the at least one computer processor, perform a method of operating the MRI apparatus to acquire diffusion-weighted images, the method comprising:
        selecting a first set of diffusion gradient vectors, each of diffusion gradient vectors in the first set having a constant gradient strength and corresponding to a first non-zero b-value, wherein the directions of the diffusion gradient vectors in the first set are distributed on a surface of a first sphere having a first radius;
        defining a cube of constant echo image time (TE) that encloses the first sphere, wherein the cube of constant TE comprises faces and edges, and a volume inside the cube of constant TE defines a volume within which any diffusion gradient vector located therein can be applied without increasing TE; and
        selecting a second set of diffusion gradient vectors, each of the diffusion gradient vectors in the second set being located within the cube of constant TE, wherein at least one of the diffusion gradient vectors in the second set corresponds to a second non-zero b-value different from the first non-zero b-value, wherein at least one diffusion gradient vector in the second set extends to a face of the cube of constant TE without also extending to an edge of the cube of constant TE, and/or at least one diffusion gradient vector in the second set extends to a point within the cube of constant TE without extending to a face or an edge of the cube of constant TE; and acquiring the diffusion-weighted images using a gradient encoding scheme including the gradients corresponding to each of the diffusion gradient vectors in the first and second sets.

14. The magnetic resonance apparatus of claim 13, wherein at least one first diffusion gradient vector in the second set extends to a face of the cube of constant TE without also extending to an edge of the cube of constant TE and at least one second diffusion gradient vector in the second set extends to a point within the cube of constant TE without extending to a face or an edge of the cube of constant TE.

15. The magnetic resonance apparatus of claim 13, wherein each of the diffusion gradient vectors in the second set extends to one of the faces of the cube of constant TE without also extending to and edge of the cube of constant TE.

16. The magnetic resonance apparatus of claim 13, wherein each of the diffusion gradient vectors in the second set extends to a point within the cube of constant TE without extending to a face or an edge of the cube of constant TE.

17. The magnetic resonance apparatus of claim 13, wherein the diffusion gradient vectors in the first set are uniformly distributed on the surface of the first sphere.

18. The magnetic resonance apparatus of claim 13, wherein selecting the second set of diffusion gradient vectors comprises:

defining a second sphere having a second radius larger than the first radius;

specifying a plurality of diffusion gradient vectors having directions distributed on a surface of the second sphere;

projecting each of the diffusion gradient vectors having axial directions distributed on the surface of the second sphere to a face or an edge of the cube of constant TE; and including the projected diffusion gradient vectors in the second set.

19. The magnetic resonance apparatus of claim 18, wherein selecting the second set of diffusion gradient values comprises:

defining a third sphere having a third radius smaller than the first radius and the second radius; and including in the second set, a plurality of diffusion gradient vectors having axial directions distributed on a surface of the third sphere.

20. The magnetic resonance apparatus of claim 18, wherein the second non-zero b-value is determined by multiplying the first non-zero b-value by a first value, and wherein defining the second sphere comprises defining the second sphere based, at least in part, on the second non-zero b-value.

* * * * *

UNITED STATES PATENT AND TRADEMARK OFFICE
CERTIFICATE OF CORRECTION

PATENT NO. : 10,782,376 B2
APPLICATION NO. : 14/431536
DATED : September 22, 2020
INVENTOR(S) : Simon K. Warfield et al.

Page 1 of 1

It is certified that error appears in the above-identified patent and that said Letters Patent is hereby corrected as shown below:

In the Claims

In Claim 4, Column 33, Lines 65-66:
"...wherein the diffusion gradient vectors in the first set of diffusion gradient vectors are..."

Should read:
"...wherein the diffusion gradient vectors in the first set are..."

Signed and Sealed this
Eighth Day of December, 2020

Andrei Iancu
*Director of the United States Patent and Trademark Office*